(12) United States Patent
Ritter et al.

(10) Patent No.: US 10,947,186 B2
(45) Date of Patent: Mar. 16, 2021

(54) PROCESS FOR HYDROCYANATION OF TERMINAL ALKYNES

(71) Applicant: STUDIENGESELLSCHAFT KOHLE MBH, Mülheim an der Ruhr (DE)

(72) Inventors: Tobias Ritter, Mülheim an der Ruhr (DE); Fei Ye, Mülheim an der Ruhr (DE)

(73) Assignee: STUDIENGESELLSCHAFT KOHLE MBH, Mülheim an der Ruhr (DE)

( * ) Notice: Subject to any disclaimer, the term of this patent is extended or adjusted under 35 U.S.C. 154(b) by 0 days.

(21) Appl. No.: 16/613,822

(22) PCT Filed: May 8, 2018

(86) PCT No.: PCT/EP2018/061861
§ 371 (c)(1),
(2) Date: Nov. 15, 2019

(87) PCT Pub. No.: WO2018/210631
PCT Pub. Date: Nov. 22, 2018

(65) Prior Publication Data
US 2020/0181068 A1  Jun. 11, 2020

(30) Foreign Application Priority Data
May 17, 2017  (DE) .................. 10 2017 110 771.1

(51) Int. Cl.
*C07C 253/12* (2006.01)
*B01J 31/24* (2006.01)
*C07C 255/31* (2006.01)
*C07C 255/34* (2006.01)
*C07D 213/64* (2006.01)
*C07D 333/24* (2006.01)

(52) U.S. Cl.
CPC .......... *C07C 253/12* (2013.01); *B01J 31/2409* (2013.01); *B01J 2231/322* (2013.01); *B01J 2531/0216* (2013.01); *B01J 2531/822* (2013.01); *C07C 255/31* (2013.01); *C07C 255/34* (2013.01); *C07D 213/64* (2013.01); *C07D 333/24* (2013.01)

(58) Field of Classification Search
CPC .................................................... C07C 253/12
See application file for complete search history.

(56) References Cited

PUBLICATIONS

Fitzmaurice, Neil J. et al.; "The Stereochemistry of Organomatellic Compounds XXVI*, Regio-and Stereo-Chemical Control . . . "; J. Organometallic Chemistry, 285 (1985) pp. 375-381.
Ye, Fei., et al.; "Rh-Catalyzed Anti-Markovnikov Hydrocyanation of Terminal Alkynes"; J. of the American Chemical Society, 2017 139, pp. 7184-7187.
Nicasio, M. Carmen, et al.; "Substitution and Hydrogenation Reactions of Rhodium (I)-Ethylene Complex . . . "; Inorg. Chem. 2000, 39, pp. 180-188.
Paneque, Margarita, et al.; "Step-by-Step Uncoordination of the Pyrazolyl Rings of Hydrotris(pyrazolyl)borate . . . "; Chem. Euro. J. 2001, 7, No. 18, pp. 3868-3879.

*Primary Examiner* — Golam M Shameem
(74) *Attorney, Agent, or Firm* — Norris McLaughlin, P.A.

(57) ABSTRACT

The present invention refers to a process for a Rh-catalyzed Anti-Markovnikov hydrocyanation of terminal alkynes which process discloses, for the first time, the highly stereo- and regio-selective hydrocyanation of terminal alkynes to furnish E-configured alkenyl nitriles and the catalyst used in the present process.

7 Claims, No Drawings

PROCESS FOR HYDROCYANATION OF TERMINAL ALKYNES

This application is a 371 of PCT/EP2018/061861, filed May 8, 2018, which claims foreign priority benefit under 35 U.S.C. § 119 of German Patent Application No. 10 2017 110 771.1, filed May 17, 2017, the disclosures of which are incorporated herein by reference.

gives access to aliphatic nitriles but failed to provide linear alkenyl nitriles.

Here, the inventors report the first stereo- and regioselective hydrocyanation of terminal acetylenes to furnish substituted trans acrylonitriles, for both aromatic and aliphatic substrates as shown in Scheme 1. The hydrocyanation reaction can be performed with acetone cyanohydrin, which the inventors considered a practical alternative to HCN.

Scheme 1. Rh-Catalyzed Anti-Markovnikov Hydrocyanation of Terminal Alkynes

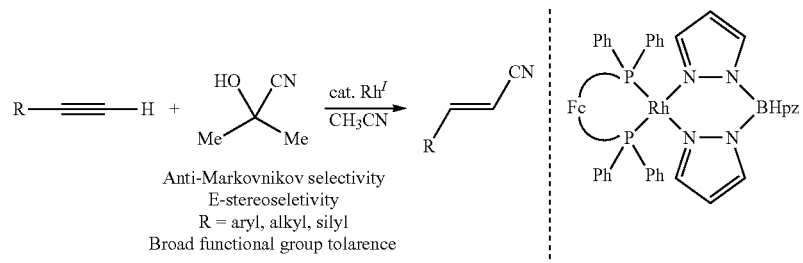

Anti-Markovnikov selectivity
E-stereoseletivity
R = aryl, alkyl, silyl
Broad functional group tolarence The present invention refers to a process for hydrocyanation of terminal alkynes and the catalyst used in the inventive process. More particularly, the invention refers to a process for a Rh-catalyzed Anti-Markovnikov hydrocyanation of terminal alkynes whereby the process discloses, for the first time, the highly stereo- and regio-selective hydrocyanation of terminal alkynes to furnish E-configured alkenyl nitriles. With the inventive process, acrylonitriles can be accessed on gram scale with broad substrate scope and functional group tolerance, and the hydrocyanation reaction may employ acetone cyanohydrin as a simple practical alternative to HCN gas which is generally also suitable as —CN source.

Transition-metal-mediated hydrocyanation across carbon-carbon multiple bond has been established as one of the most direct approaches to produce nitriles. Products of hydrocyanation are versatile building blocks in material science, natural product synthesis and the pharmaceutical industry. The nitrile groups can be further transformed to aldehydes, acids, amides as well as heterocycles, and can also be exploited for α- or β-functionalization reactions due to its electron-withdrawing nature.

Reported transition-metal-catalyzed hydrocyanation of terminal alkynes gives rise to branched alkenyl nitriles through Markovnikov addition. In very few cases, linear products have been observed, but in low yield and with low functional group tolerance. In the state of art, there is no general catalytic reaction for anti-Markovnikov hydrocyanation of alkynes.

Products of anti-Markovnikov hydrocyanation of alkynes are useful building blocks, but Ni-catalyzed addition of hydrogen cyanide to alkynes occurs with Markovnikov selectivity. For arylacetylenes, reported hydrocyanation reactions provide mixtures of both linear and branched isomers in a maximum of 35% yield with either HCN or acetone cyanohydrin as HCN source. From terminal alkynes, substituted acrylonitriles are typically prepared in a two steps protocol, via hydroalumination or hydroboronation followed by cyanation. The cyanation requires toxic cyanogen or excess CuCN. A Ni(O)-catalyzed reversible alkene-nitrile interconversion has also been reported, which Thus, the present invention refers to a process for hydrocyanation of terminal alkynes wherein a terminal alkyne (I) is reacted with a —CN source selected from HCN and/or cyanohydrine (II) in the presence of a Rh-complex whereby an E-alkenyl nitrile (III) is obtained as shown in the following Scheme:

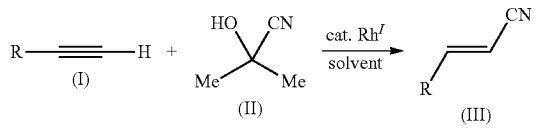

wherein R is i) a straight chain, branched chain or cyclic aliphatic $C_1$ to $C_{20}$ hydrocarbon, optionally having one or more unsaturated bonds, $C_3$-$C_8$-heterocycloalkyl, $C_6$ to $C_{20}$ aryl, ($C_1$-$C_6$)-alkyl-$C_6$ to $C_{20}$-aryl, ($C_1$-$C_6$)-alkyl-$C_5$ to $C_{20}$-heteroaryl, each hydrocarbon optionally being substituted by one or more groups selected from $C_1$ to $C_{20}$ straight chain, branched chain or cyclic aliphatic hydrocarbons, optionally having one or more unsaturated bonds, $C_3$-$C_8$-heterocycloalkyl, $C_6$ to $C_{20}$ aryl, ($C_1$-$C_6$)-alkyl-$C_6$ to $C_{20}$-aryl, $C_5$ to $C_{20}$-heteroaryl, ($C_1$-$C_6$)-alkyl-$C_5$ to $C_{20}$-heteroaryl or heterosubstituents; or ii) —SiR$^I$R$^{II}$R$^{III}$, wherein R$^I$, R$^{II}$ and R$^{III}$ may be same or different and each stands for a straight chain, branched chain or cyclic aliphatic $C_1$ to $C_{20}$ hydrocarbon, optionally having one or more unsaturated bonds, $C_3$-$C_8$-heterocycloalkyl, $C_6$ to $C_{20}$ aryl, ($C_1$-$C_6$)-alkyl-$C_6$ to $C_{20}$-aryl, ($C_1$-$C_6$)-alkyl-$C_5$ to $C_{20}$-heteroaryl, each hydrocarbon optionally being substituted by one or more groups selected from $C_1$ to $C_{20}$ straight chain, branched chain or cyclic aliphatic hydrocarbons, optionally having one or more unsaturated bonds, $C_3$-$C_8$-heterocycloalkyl, $C_6$ to $C_{20}$ aryl, ($C_1$-$C_6$)-alkyl-$C_6$ to $C_{20}$-aryl, ($C_1$-$C_6$)-alkyl-$C_5$ to $C_{20}$-heteroaryl or heterosubstituents;

wherein $R_1$ and $R_2$ may be same or different and each stands for a straight chain, branched chain or cyclic aliphatic $C_1$ to $C_{20}$ hydrocarbon, optionally having one or more unsaturated bonds, $C_3$-$C_8$-heterocycloalkyl, $C_6$ to $C_{20}$ aryl, ($C_1$-$C_6$)-alkyl-$C_6$ to $C_{20}$-aryl, ($C_1$-$C_6$)-alkyl-$C_5$ to $C_{20}$-heteroaryl, each hydrocarbon optionally being substituted by one or more groups selected from $C_1$ to $C_{20}$ straight chain, branched chain or cyclic aliphatic hydrocarbons, optionally having one or more unsaturated bonds, $C_3$-$C_8$-heterocycloalkyl, $C_6$ to $C_{20}$ aryl, $(C_1$-$C_6)$-alkyl-$C_6$ to $C_{20}$-aryl, $(C_1$-$C_6)$-alkyl-$C_5$ to $C_{20}$-heteroaryl or heterosubstituents;

wherein cat Rh$^I$ stands for a Tp-Rhodium complex with a mono- or bidentate phosphine, wherein solvent stands for a aprotic polar organic solvent preferably selected from aceton, acetonitrile, DMF, DMSO, or mixtures thereof.

In one embodiment, R is a straight chain, branched chain or cyclic aliphatic $C_1$ to $C_{20}$ hydrocarbon, optionally having one or more unsaturated bonds, $C_6$ to $C_{20}$ aryl, $(C_1$-$C_6)$-alkyl-$C_6$ to $C_{20}$-aryl, each hydrocarbon optionally being substituted by one or more heterosubstituents.

In one embodiment, $R_1$ and $R_2$ may be same or different and each stands for is a straight chain, branched chain or cyclic aliphatic $C_1$ to $C_{20}$ hydrocarbon, optionally having one or more unsaturated bonds, $C_6$ to $C_{20}$ aryl, $(C_1$-$C_6)$-alkyl-$C_6$ to $C_{20}$-aryl, each hydrocarbon optionally being substituted by one or more heterosubstituents.

The Tp-Rhodium complex with a bidentate phosphine (TpRhBidP), whereby the residues of the Tp ((tris(1-pyrazolyl)borate anion) and/or the bidentate phosphine ligand are optionally substituted with electro-donating substituent(s) such as $C_1$ to $C_6$ alkyl or —O-alkyl, —NH-alkyl or —N-dialkyl, may be prepared from the respective Tp-Rh-COD or TpRh($C_2H_4$)$_2$.

Generally, any mono- or bidentate phosphine ligand, preferably any bidentate phosphine ligand, may be used to form the Tp-Rh-BiP complex and exemplarily, dppf (1,1'-bis(diphenylphosphino)ferrocene), dppm (1-bis(diphenylphosphino)methane), dppe (bis(diphenylphosphino)ethan), xantphos (4,5-bis(diphenylphosphino)-9,9-dimethylxanthene), PCy$_3$ (tricyclohexylphosphine), PPh$_3$ (triphenylphosphine), BINAP (2,2'-bis(diphenylphosphino)-1,1'-binaphthyl), and DPE-phos (bis[2-(diphenylphosphino)phenyl]ether are useful as ligands.

The present invention therefore also refers to a Tp-Rhodium complex with a mono- or preferably bidentate phosphine (TpRhBidP), wherein the BidP is preferably selected from dppf (1,1'-bis(diphenylphosphino)ferrocene), dppm (1-bis(diphenylphosphino)methane), dppe (bis(diphenylphosphino)ethan), xantphos (4,5-bis(diphenylphosphino)-9,9-dimethylxanthene), PCy$_3$ (tricyclohexylphosphine), PPh$_3$ (triphenylphosphine), BINAP (2,2'-bis(diphenylphosphino)-1,1'-binaphthyl), and DPE-phos (bis[2-(diphenylphosphino)phenyl]ether In one embodiment, the TpRhBidP complex is selected from TpRh(dppf), TpRh(dpe-phos).

In a further embodiment, the invention also refers to the use thereof as a catalyst, preferably in a process for hydrocyanation of terminal alkynes.

In the inventive process, the choice of the solvent is not critical as long as it is a aprotic polar organic solvent selected from acetonitrile, chlorinated hydrocarbons, or mixtures thereof. The reaction conditions are also not critical and the reaction is usually carried out at an elevated temperature between 30° and 130° C., preferably 70° to 130° C., under reaction pressure and optionally under an inert gas atmosphere.

In the above formulae, R may be selected from hydrogen, $C_1$ to $C_{20}$ straight chain, branched chain or cyclic aliphatic hydrocarbons, optionally having one or more unsaturated bonds such as $C_1$-$C_{20}$-alkyl, $C_2$-$C_{20}$-alkenyl or $C_2$-$C_{20}$-alkinyl, $C_3$-$C_8$-heterocycloalkyl or $C_6$ to $C_{20}$ aromatic hydrocarbon and partially arene-hydrogenated forms such as aryl, aryl-$(C_1$-$C_6)$-alkyl, heteroaryl-$(C_1$-$C_6)$-alkyl, each hydrocarbon optionally being substituted by one or more groups selected from $C_1$ to $C_{20}$ straight chain, branched chain or cyclic aliphatic hydrocarbons, optionally having one or more unsaturated bonds such as $C_1$-$C_{20}$-alkyl, $C_2$-$C_{20}$-alkenyl or $C_2$-$C_{20}$-alkinyl, $C_3$-$C_8$-heterocycloalkyl or $C_6$ to $C_{20}$ aromatic hydrocarbon and partially arene-hydrogenated forms such as aryl, aryl-$(C_1$-$C_6)$-alkyl, heteroaryl-$(C_1$-$C_6)$-alkyl or heterosubstituents, In the above formulae (I), $R^1$ to $R^4$ may be selected each from $C_1$ to $C_{20}$ straight chain, branched chain or cyclic aliphatic hydrocarbons, optionally having one or more unsaturated bonds such as $C_1$-$C_{20}$-alkyl, $C_2$-$C_{20}$-alkenyl or $C_2$-$C_{20}$-alkinyl, $C_3$-$C_8$-heterocycloalkyl or $C_6$ to $C_{20}$ aromatic hydrocarbon and partially arene-hydrogenated forms such as aryl, aryl-$(C_1$-$C_6)$-alkyl, heteroaryl-$(C_1$-$C_6)$-alkyl, each hydrocarbon optionally being substituted by one or more groups selected from $C_1$ to $C_{20}$ straight chain, branched chain or cyclic aliphatic hydrocarbons, optionally having one or more unsaturated bonds such as $C_1$-$C_{20}$-alkyl, $C_2$-$C_{20}$-alkenyl or $C_2$-$C_{20}$-alkinyl, or $C_6$ to $C_{20}$ aromatic hydrocarbon and partially arene-hydrogenated forms such as aryl, aryl-$(C_1$-$C_6)$-alkyl, heteroaryl-$(C_1$-$C_6)$-alkyl or heterosubstituents.

—SiR$^I$R$^{II}$R$^{III}$, wherein R$^I$, R$^{II}$ and R$^{III}$ may be same or different and each stand for hydrogen, halogen, a straight chain, branched chain or cyclic aliphatic $C_1$ to $C_{20}$ hydrocarbon, optionally having one or more unsaturated bonds, $C_3$-$C_8$-heterocycloalkyl or $C_6$ to $C_{20}$ aromatic hydrocarbons, $(C_1$-$C_6)$-alkyl-$C_6$ to $C_{20}$ aromatic hydrocarbons, heteroaryl-$(C_1$-$C_6)$-alkyl, each hydrocarbon optionally being substituted by one or more groups selected from $C_1$ to $C_{20}$ straight chain, branched chain or cyclic aliphatic hydrocarbons, optionally having one or more unsaturated bonds such as $C_1$-$C_{20}$-alkyl, $C_2$-$C_{20}$-alkenyl or $C_2$-$C_{20}$-alkinyl, $C_3$-$C_8$-heterocycloalkyl or $C_6$ to $C_{20}$ aromatic hydrocarbon and partially arene-hydrogenated forms such as aryl, aryl-$(C_1$-$C_6)$-alkyl, heteroaryl-$(C_1$-$C_6)$-alkyl or heterosubstituents.

A heterosubstituent as defined according to the invention can be selected from OH, F, Cl, Br, I, CN, NO$_2$, SO$_3$H, a monohalogenomethyl group, a dihalogenomethyl group, a trihalogenomethyl group, CF(CF$_3$)$_2$, SF$_5$, amine bound through N atom, —O-alkyl (alkoxy), —O-aryl, —O—SiR$^S_3$, S—R$^S$, S(O)—R$^S$, S(O)$_2$—R$^S$, COOH, CO$_2$—R$^S$, amide, bound through C or N atom, formyl group, C(O)—R$^S$, COOM, where M may be a metal such as Na or K. R$^S_3$ may be, independently from each other, the same or different and may be each an aliphatic, heteroaliphatic, aromatic or heteroaromatic $C_1$-$C_{20}$ hydrocarbon, each optionally being further substituted by one or more heterosubstituents.

The term "aliphatic" includes both saturated and unsaturated, straight chain (i.e., unbranched), branched, acyclic, cyclic, or polycyclic aliphatic hydrocarbons, which are optionally substituted with one or more functional groups. As will be appreciated by one of ordinary skill in the art, "aliphatic" is intended herein to include, but is not limited to, alkyl, alkenyl, alkynyl, cycloalkyl, cycloalkenyl, and cycloalkynyl moieties. Thus, the term "alkyl" includes straight, branched and acyclic alkyl groups. An analogous convention applies to other generic terms such as "alkenyl", "alkynyl", and the like. Furthermore, the terms "alkyl", "alkenyl", "alkynyl", and the like encompass both substituted and unsubstituted groups. In certain embodiments, "lower alkyl" is used to indicate those alkyl groups (acyclic, substituted, unsubstituted, branched or unbranched) having 1-6 carbon atoms.

As used herein, "alkyl" refers to a radical of a straight-chain or branched saturated hydrocarbon group having from 1 to 20 carbon atoms ("$C_{1-20}$ alkyl"). In some embodiments, an alkyl group has 1 to 10 carbon atoms ("$C_{1-10}$ alkyl"). In some embodiments, an alkyl group has 1 to 9 carbon atoms ("$C_{1-9}$ alkyl"). In some embodiments, an alkyl group has 1 to 8 carbon atoms ("$C_{1-8}$ alkyl"). In some embodiments, an alkyl group has 1 to 7 carbon atoms ("$C_{1-7}$ alkyl"). In some embodiments, an alkyl group has 1 to 6 carbon atoms ("$C_{1-6}$ alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). In some embodiments, an alkyl group has 2 to 6 carbon atoms ("$C_{2-6}$ alkyl"). Examples of $C_{1-6}$ alkyl groups include methyl ($C_1$), ethyl ($C_2$), n-propyl ($C_3$), isopropyl ($C_3$), n-butyl ($C_4$), tert-butyl ($C_4$), sec-butyl ($C_4$), iso-butyl ($C_4$), n-pentyl ($C_5$), 3-pentanyl ($C_5$), amyl ($C_5$), neopentyl ($C_5$), 3-methyl-2-butanyl ($C_5$), tertiary amyl ($C_5$), and n-hexyl ($C_6$). Additional examples of alkyl groups include n-heptyl ($C_7$), n-octyl ($C_8$) and the like. Unless otherwise specified, each instance of an alkyl group is independently unsubstituted (an "unsubstituted alkyl") or substituted (a "substituted alkyl") with one or more substituents. In certain embodiments, the alkyl group is an unsubstituted $C_{1-10}$ alkyl (e.g., —$CH_3$). In certain embodiments, the alkyl group is a substituted $C_{1-10}$ alkyl.

When a range of values is listed, it is intended to encompass each value and sub-range within the range. For example "$C_{1-6}$" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$.

"Alkynyl" refers to a radical of a straight-chain or branched hydrocarbon group having from 2 to 20 carbon atoms, and one or more carbon-carbon triple bonds ("$C_{2-20}$ alkynyl"). In some embodiments, an alkynyl group has 2 to 10 carbon atoms ("$C_{2-10}$ alkynyl"). In some embodiments, an alkynyl group has 2 to 9 carbon atoms ("$C_{2-9}$ alkynyl"). In some embodiments, an alkynyl group has 2 to 8 carbon atoms ("$C_{2-8}$ alkynyl"). In some embodiments, an alkynyl group has 2 to 7 carbon atoms ("$C_{2-7}$ alkynyl"). In some embodiments, an alkynyl group has 2 to 6 carbon atoms ("$C_{2-6}$ alkynyl"). In some embodiments, an alkynyl group has 2 to 5 carbon atoms ("$C_{2-5}$ alkynyl"). In some embodiments, an alkynyl group has 2 to 4 carbon atoms ("$C_{2-4}$ alkynyl"). In some embodiments, an alkynyl group has 2 to 3 carbon atoms ("$C_{2-3}$ alkynyl"). In some embodiments, an alkynyl group has 2 carbon atoms ("$C_2$ alkynyl"). The one or more carbon-carbon triple bonds can be internal (such as in 2-butynyl) or terminal (such as in 1-butynyl). Examples of $C_{2-4}$ alkynyl groups include, without limitation, ethynyl ($C_2$), 1-propynyl ($C_3$), 2-propynyl ($C_3$), 1-butynyl ($C_4$), 2-butynyl ($C_4$), and the like. Examples of $C_{2-6}$ alkynyl groups include the aforementioned $C_{2-4}$ alkynyl groups as well as pentynyl ($C_5$), hexynyl ($C_6$), and the like. Additional examples of alkynyl include heptynyl ($C_7$), octynyl ($C_8$), and the like. Unless otherwise specified, each instance of an alkynyl group is independently optionally substituted, i.e., unsubstituted (an "unsubstituted alkynyl") or substituted (a "substituted alkynyl") with one or more substituents. In certain embodiments, the alkynyl group is unsubstituted $C_{2-10}$ alkynyl. In certain embodiments, the alkynyl group is substituted $C_{2-10}$ alkynyl.

"Heterocyclic" refers to a radical of a 3- to 14-membered non-aromatic ring system having ring carbon atoms and 1 to 4 ring heteroatoms, wherein each heteroatom is independently selected from nitrogen, oxygen, sulfur, boron, phosphorus, and silicon ("3-14 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or a fused, bridged, or spiro ring system, such as a bicyclic system ("bicyclic heterocyclyl"), and can be saturated or can be partially unsaturated. Heterocyclyl bicyclic ring systems can include one or more heteroatoms in one or both rings. "Heterocyclyl" also includes ring systems wherein the heterocyclic ring, as defined above, is fused with one or more carbocyclyl groups wherein the point of attachment is either on the carbocyclyl or heterocyclic ring, or ring systems wherein the heterocyclic ring, as defined above, is fused with one or more aryl or heteroaryl groups, wherein the point of attachment is on the heterocyclic ring, and in such instances, the number of ring members continue to designate the number of ring members in the heterocyclic ring system. Unless otherwise specified, each instance of heterocyclyl is independently optionally substituted, i.e., unsubstituted (an "unsubstituted heterocyclyl") or substituted (a "substituted heterocyclyl") with one or more substituents. In certain embodiments, the heterocyclyl group is unsubstituted 3-14 membered heterocyclyl. In certain embodiments, the heterocyclyl group is substituted 3-14 membered heterocyclyl.

"Aryl" refers to a radical of a monocyclic or polycyclic (e.g., bicyclic or tricyclic) 4n+2 aromatic ring system (e.g., having 6, 10, or 14 pi electrons shared in a cyclic array) having 6-14 ring carbon atoms and zero heteroatoms provided in the aromatic ring system ("$C_{6-14}$ aryl"). In some embodiments, an aryl group has six ring carbon atoms ("$C_6$ aryl"; e.g., phenyl). In some embodiments, an aryl group has ten ring carbon atoms ("$C_{10}$ aryl"; e.g., naphthyl such as 1-naphthyl and 2-naphthyl). In some embodiments, an aryl group has fourteen ring carbon atoms ("$C_{14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Unless otherwise specified, each instance of an aryl group is independently optionally substituted, i.e., unsubstituted (an "unsubstituted aryl") or substituted (a "substituted aryl") with one or more substituents. In certain embodiments, the aryl group is unsubstituted $C_{6-14}$ aryl. In certain embodiments, the aryl group is substituted $C_{6-14}$ aryl.

"Aralkyl" is a subset of alkyl and aryl and refers to an optionally substituted alkyl group substituted by an optionally substituted aryl group. In certain embodiments, the aralkyl is optionally substituted benzyl. In certain embodiments, the aralkyl is benzyl. In certain embodiments, the aralkyl is optionally substituted phenethyl. In certain embodiments, the aralkyl is phenethyl.

"Heteroaryl" refers to a radical of a 5-14 membered monocyclic or bicyclic 4n+2 aromatic ring system (e.g., having 6 or 10 pi electrons shared in a cyclic array) having ring carbon atoms and 1-4 ring heteroatoms provided in the aromatic ring system, wherein each heteroatom is independently selected from nitrogen, oxygen, and sulfur ("5-14 membered heteroaryl"). In heteroaryl groups that contain one or more nitrogen atoms, the point of attachment can be a carbon or nitrogen atom, as valency permits. Heteroaryl bicyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused (aryl/heteroaryl) ring system. Bicyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl).

In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur. Unless otherwise specified, each instance of a heteroaryl group is independently optionally substituted, i.e., unsubstituted (an "unsubstituted heteroaryl") or substituted (a "substituted heteroaryl") with one or more substituents. In certain embodiments, the heteroaryl group is unsubstituted 5-14 membered heteroaryl. In certain embodiments, the heteroaryl group is substituted 5-14 membered heteroaryl.

Thus, aliphatic hydrocarbons including alkyl, alkenyl and alkinyl may comprise straight-chain, branched and cyclic hydrocarbons.

Heteroaliphatic is a hydrocarbon including alkyl, alkenyl and alkinyl which may comprise straight-chain, branched and cyclic hydrocarbons with one or more carbon atoms substituted with a heteroatom.

In more detail, $C_1$-$C_{20}$-Alkyl can be straight chain or branched and has 1, 2, 3, 4, 5, 6, 7, 8, 9, 10, 11, 12, 13, 14, 15, 16, 17, 18, 19 or 20 carbon atoms. Alkyl might be $C_1$-$C_6$-alkyl, in particular methyl, ethyl, propyl, isopropyl, butyl, isobutyl, sec-butyl or tert-butyl, likewise pentyl, 1-, 2- or 3-methylpropyl, 1,1-, 1,2- or 2,2-dimethylpropyl, 1-ethylpropyl, hexyl, 1-, 2, 3- or 4-methylpentyl, 1,1-, 1,2-, 1,3-, 2,2-, 2,3- or 3,3-dimethylbutyl, 1- or 2-ethylbutyl, 1-ethyl-1-methylpropyl, 1-ethyl-2-methylpropyl, 1,1,2- or 1,2,2-trimethylpropyl.

Cycloalkyl might be cyclopropyl, cyclobutyl, cyclopentyl, cyclohexyl or cycloheptyl.

Alkenyl might be $C_2$-$C_{20}$ alkenyl. Alkinyl might be $C_2$-$C_{20}$ alkinyl.

Said unsaturated alkenyl- or alkinyl groups can be used for linking the inventive compounds to a carrier such as a polymer to serve for an immobilized catalyst.

Halogen is F, Cl, Br or I.

Alkoxy is preferably $C_2$-$C_{10}$ alkoxy such as methoxy, ethoxy, propoxy, tert-butoxy etc.

$C_3$-$C_8$-Heterocycloalkyl having one or more heteroatoms selected from among N, O and S is preferably 2,3-dihydro-2-, -3-, -4- or -5-furyl, 2,5-dihydro-2-, -3-, -4- or -5-furyl, tetrahydro-2- or -3-furyl, 1,3-dioxolan-4-yl, tetrahydro-2- or -3-thienyl, 2,3-dihydro-1-, -2-, -3-, -4- or -5-pyrrolyl, 2,5-dihydro-1-, -2-, -3-, -4- or -5-pyrrolyl, 1-, 2- or 3-pyrrolidinyl, tetrahydro-1-, -2- or -4-imidazolyl, 2,3-dihydro-1-, -2-, -3-, -4- or -5-pyrazolyl, tetrahydro-1-, -3- or -4-pyrazolyl, 1,4-dihydro-1-, -2-, -3- or -4-pyridyl, 1,2,3,4-tetrahydro-1-, -2-, -3-, -4-, -5- or -6-pyridyl, 1-, 2-, 3- or 4-piperidinyl, 2-, 3- or 4-morpholinyl, tetrahydro-2-, -3- or -4-pyranyl, 1,4-dioxanyl, 1,3-dioxan-2-, -4- or -5-yl, hexahydro-1-, -3- or -4-pyridazinyl, hexahydro-1-, -2-, -4- or -5-pyrimidinyl, 1-, 2- or 3-piperazinyl, 1,2,3,4-tetrahydro-1-, -2-, -3-, -4-, -5-, -6-, -7- or -8-quinolyl, 1,2,3,4-tetrahydro-1-, -2-, -3-, -4-, -5-, -6-, -7- or -8-isoquinolyl, 2-, 3-, 5-, 6-, 7- or 8-3,4-dihydro-2H-benzo-1,4-oxazinyl.

Optionally substituted means unsubstituted or monosubstituted, disubstituted, trisubstituted, tetrasubstituted, pentasubstituted, or even further substituted for each hydrogen on the hydrocarbon.

Aryl might be phenyl, naphthyl or biphenyl.

Arylalkyl might be benzyl.

Heteroaryl having one or more heteroatoms selected from among N, O and S is preferably 2- or 3-furyl, 2- or 3-thienyl, 1-, 2- or 3-pyrrolyl, 1-, 2-, 4- or 5-imidazolyl, 1-, 3-, 4- or 5-pyrazolyl, 2-, 4- or 5-oxazolyl, 3-, 4- or 5-isoxazolyl, 2-, 4- or 5-thiazolyl, 3-, 4- or 5-isothiazolyl, 2-, 3- or 4-pyridyl, 2-, 4-, 5- or 6-pyrimidinyl, also preferably 1,2,3-triazol-1-, -4- or -5-yl, 1,2,4-triazol-1-, -3- or -5-yl, 1- or 5-tetrazolyl, 1,2,3-oxadiazol-4- or -5-yl, 1,2,4-oxadiazol-3- or -5-yl, 1,3,4-thiadiazol-2- or -5-yl, 1,2,4-thiadiazol-3- or -5-yl, 1,2,3-thiadiazol-4- or -5-yl, 3- or 4-pyridazinyl, pyrazinyl, 1-, 2-, 3-, 4-, 5-, 6- or 7-Indolyl, 4- or 5-isoindolyl, 1-, 2-, 4- or 5-benz-imidazolyl, 1-, 3-, 4-, 5-, 6- or 7-benzopyrazolyl, 2-, 4-, 5-, 6- or 7-benzoxazolyl, 3-, 4-, 5-, 6- or 7-benzisoxazolyl, 2-, 4-, 5-, 6- or 7-benzothiazolyl, 2-, 4-, 5-, 6- or 7-benzisothiazolyl, 4-, 5-, 6- or 7-benz-2,1,3-oxadiazolyl, 2-, 3-, 4-, 5-, 6-, 7- or 8-quinolyl, 1-, 3-, 4-, 5-, 6-, 7- or 8-isoquinolyl, 3-, 4-, 5-, 6-, 7- or 8-cinnolinyl, 2-, 4-, 5-, 6-, 7- or 8-quinazolinyl, 5- or 6-quinoxalinyl, 2-, 3-, 5-, 6-, 7- or 8-2H-benzo-1,4-oxazinyl, also preferably 1,3-benzodioxol-5-yl, 1,4-benzodioxan-6-yl, 2,1,3-benzothiadiazol-4- or -5-yl or 2,1,3-benzoxadiazol-5-yl.

EXPERIMENTAL PART

As shown in the Experimental part, functional groups including esters, halides, ketones, alcohols, trimethylsilyl, pinacolborate, phenols and amides are tolerated in the reaction (Table 1). Both electron-poor and -rich arylacetylenes are suitable substrates. Substitution in the ortho-position of the arenes did not hinder efficient hydrocyanation (2l, 2o). Unprotected anilines yielded less than 5% yield as essayed by GC-MS and NMR spectroscopy, possibly due to amine protonation; however, protected amines as well as amides are tolerated (2h, 2j). Alcohols are also tolerated (2n, 2p). Furthermore, heterocycles such as thiophene (2r) and pyridine (2u) are suitable substrates for the hydrocyanation reaction. Preparation on 1 mmol scale of 2n worked smoothly to give slightly higher yield of product. Within the limits of detection, all products were obtained with complete stereoselectivity, and with complete preference for anti-Markovnikov addition over Markovnikov addition as judged by GC-MS. For example, the inventors have established that in the synthesis of 2g no other volatile compounds, especially no isomer of 2g, are formed.

TABLE 1

Rh(I)-Catalyzed Anti-Markovnikov Hydrocyanation of Aromatic Terminal Alkynes with Acetone Cyanohydrin[a,b]

Ar—≡—H (1a-u) + HO-C(Me)(Me)-CN → (TpRh(COD) 7.5 mol %, dppf 7.5 mol %, CH$_3$CN, 110° C., 12 h) → Ar-CH=CH-CN (2a-u)

2a, 88%

2b, 78% (MeO-)

2c, 69%[c,d] (Ph-)

2d, 92% (tBu-)

2e, 73%[d] (TMS-)

2f, 68%[d] (Bpin-)

2g, 62% 1.0 mmol, 66% (F-)

2h, 51%[c] (H$_2$N-C(O)-)

2i, 68% (NC-)

2j, 65%[c,e] (Fmoc-NH-)

2k, 79% (o-Me)

2l, 78% (o-CO$_2$Me)

2m, 67% (o-Cl)

2n, 65% 1.0 mmol, 71% (o-CH$_2$OH)

2o, 82%[c,d] (2,4,6-Me$_3$)

2p, 78% (m-HO)

2q, 64%

2r, 70% 1.0 mmol, 75%

TABLE 1-continued

Rh(I)-Catalyzed Anti-Markovnikov Hydrocyanation of Aromatic Terminal Alkynes with Acetone Cyanohydrin[a,b]

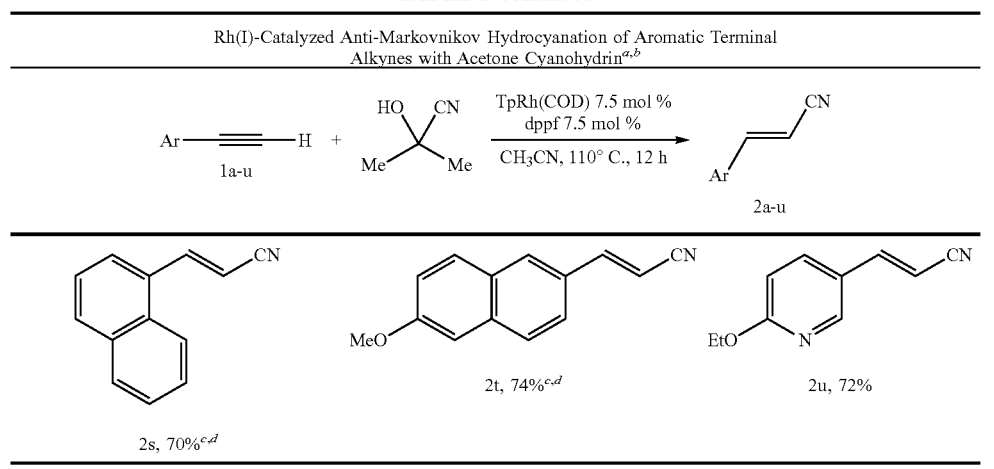

[a] Reaction conditions: 1a-u (0.20 mmol), acetone cyanohydrin (0.20 mmol, 1.0 eq), TpRh(COD) (7.5 mol %), ligand (7.5 mol %), CH$_3$CN (1.0 mL), 110° C., 12 h.
[b] Isolated yield.
[c] CH$_3$CN (1.5 mL).
[d] Acetone cyanohydrin (0.24 mmol, 1.2 eq).
[e] 17% of alkynes were recovered.

In addition to hydrocyanation of arylacetylenes, both alkyl- and silyl-substituted alkynes participated in selective hydrocyanation upon modification of the ancillary ligand (DPE-phos instead of dppf) (Table 3). Anti-Markovnikov selectivity was observed here as well, albeit in lower magnitude than what was observed for the aromatic alkynes (4:1-20:1). Both, the alkynyl substituent size and electronic properties influence the regioselectivity. Higher anti-Markovnikov selectivity was obtained with substrates bearing bulkier substituents (5b vs 5c, 5f), and with conjugated enynes (5d vs 5e), which possibly may be explained by faster formation of Rh-vinylidene intermediates (vide infra). Silyl protected acetylene gave product in >20:1 regioselectivity (5g).

TABLE 3

Rh(I)-Catalyzed Anti-Markovnikov Hydrocyanation of Aliphatic Terminal Alkynes with Acetone Cyanohydrin[a,b]

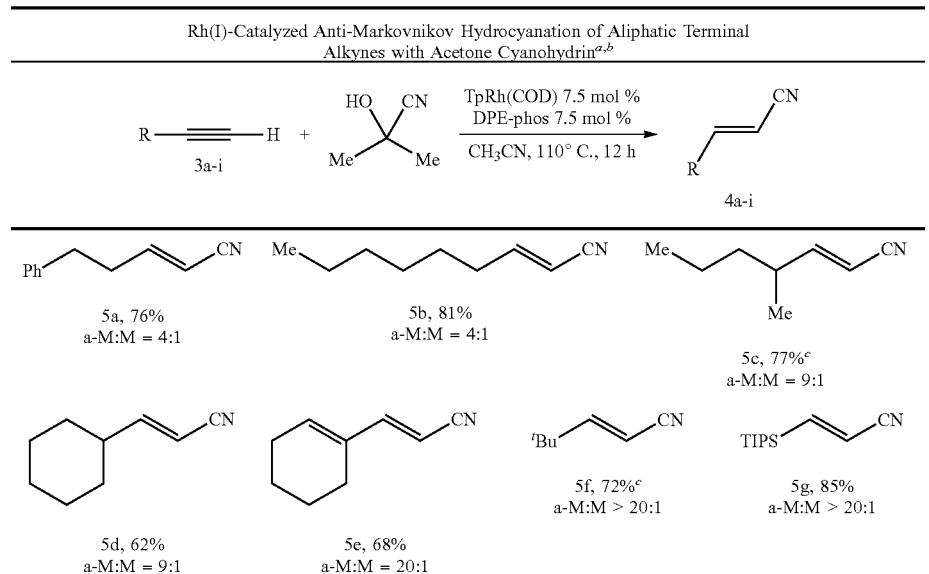

[a] Reaction conditions: 4a-g (0.20 mmol), acetone cyanohydrin (0.20 mmol 1.0 eq), TpRh(COD) (7.5 mol %), DPE-phos (7.5 mol %), CH$_3$CN (1.0 mL), 110° C., 12 h.
[b] Isolated yield.
[c] NMR yield due to volatility of the products.
a-M = anti-Markovnikov;
M = Markovnikov addition.

To gain preliminary insight into the mechanism, the inventors observed the formation of the active catalyst TpRh(dppf) upon reaction of dppf and TpRh(COD), which itself was made from commercial [Rh(COD)Cl]2 and KTp.[10] Hydrocyanation with TpRh(dppf) as catalyst afforded nearly identical results as compared to the reactions, in which the active catalyst was prepared in situ from TpRh(COD) and dppf (Scheme 2).

13

Scheme 2. Rh(I) Catalyst Synthesis and X-ray Structure

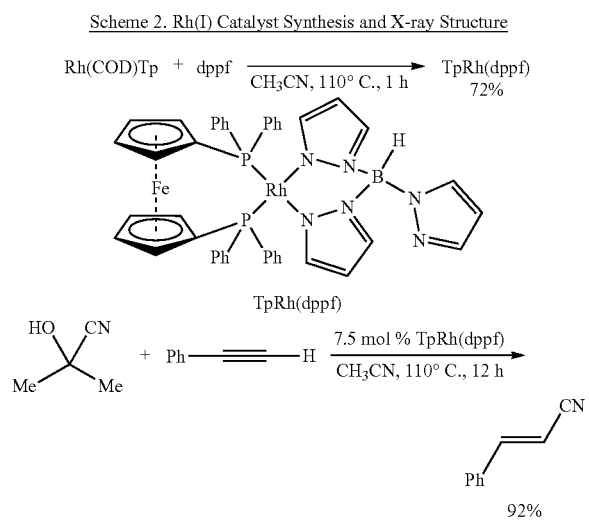

As detailed above, the present invention refers to a process for the straightforward synthesis of substituted trans acrylonitriles through Rh-catalyzed anti-Markovnikov addition of HCN to terminal alkynes. Mixing of commercially available phenylacetylene, acetone cyanohydrin, dppf and TpRh(COD) (Tp=(tris(1-pyrazolyl)borohydride)) in MeCN and heating at 110° C. afforded the desired cinnamonitrile (2a) in 88% yield, without the formation, within limits of detection, of the Z-isomer or the Markovnikov product (Table 1). Nearly identical results were obtained by using TpRh(C$_2$H$_4$)$_2$ instead of TpRh(COD) as catalyst precursor. Because the inventors could prepare TpRh(COD) in higher yield than TpRh(C$_2$H$_4$)$_2$, they have opted to use the COD complex in their investigations. The choice of ancillary ligands is crucial for a productive and selective reaction: The Tp ligand is essential; even Tp* (tris(3,5-dimethylpyrazolyl) borohydride)) and Bp (bis(1-pyrazolyl)borohydride) were ineffective. Bidentate diphosphines performed better than monodentate phosphines, the best of which provided only 8% of product. Among the bidentate ligands evaluated, dppf performed best. A reaction temperature of 110° C. is required; no product formed below 70° C.

The invention is further illustrated by the following General Procedures and Examples. The Preparation Examples 1 refer to the preparation of various terminal alkynes which were then reacted to the trans acrylonitriles in the Inventive Examples 2(a-u) and 5.

14

General Procedure of Hydrocyanation of Arylacetylenes

Under Ar atmosphere, an oven-dried 10 mL vial was charged with TpRh(COD) (31.5 mg, 75.0 µmol, 7.50 mol %), dppf (41.5 mg, 75.0 µmol, 7.50 mol %) and MeCN (5.0 mL, c=0.2 M). Alkyne (1.00 mmol, 1.00 equiv) and acetone cyanohydrin (85.0 mg, 97.5 µL, 1.00 mmol, 1.00 equiv) were then added to the reaction mixture. The vial was sealed with a Teflon cap and moved to a preheated metal heating block (110° C.). The reaction mixture was then stirred at 110° C. for 12 hours. After cooling to 23° C., the resulting mixture was filtered through a short plug of silica gel, eluting with EtOAc. The filtrate was collected and concentrated in vacuo. The resulting residue was purified by flash column chromatography on silica gel to afford the corresponding hydrocyanated alkene.

In situ generation of the catalyst through combination of commercially available [Rh(COD)Cl]2 (3.75 µmol), KTp (15 µmol), and dppf (7.5 µmol) can also be used for productive hydrocyanation. However, the inventors observed that in situ catalyst generation afforded products in lower yield than the use of TpRh(COD) complex. For example, hydrocyanation of phenylacetylene afforded product in 45% yield with the catalyst prepared in situ, while xx % were obtained with TpRh(COD) as precatalyst. For a straightforward synthesis of TpRh(COD) (6), vide infra.

The inventors appreciate that, generally, for practical use, many scientists prefer not to use a glovebox. The transformation, as reported in this general procedure, can be carried out conveniently without the use of a glovebox. For simplicity, in the inventors' own research, the inventors have opted to execute the transformation for most compounds by using a glovebox. Control experiments showed that yields were within error of measurement if the reaction was carried out using a glovebox or not.

General Procedure of Hydrocyanation of Alkylacetylenes

Under Ar atmosphere, an oven-dried 4 mL vial was charged with TpRh(COD) (6.3 mg, 15 µmol, 7.5 mol %), DPE-phos (8.0 mg, 15 µmol, 7.5 mol %) and MeCN (1.0 mL, c=0.2 M). Alkyne (0.200 mmol, 1.00 equiv.) and acetone cyanohydrin (17.0 mg, 19.5 µL, 0.200 mmol, 1.00 equiv.) were then added to the reaction mixture. The vial was sealed with a Teflon cap and moved to a preheated metal heating block (110° C.). The reaction mixture was then stirred at 110° C. for 12 hours. After cooling to 23° C., the resulting mixture was filtered through a short plug of silica gel, eluting with EtOAc. The filtrate was collected and concentrated in vacuo. The resulting residue was purified by flash column chromatography on silica gel to afford the corresponding hydrocyanated alkene.

Isomer Analysis

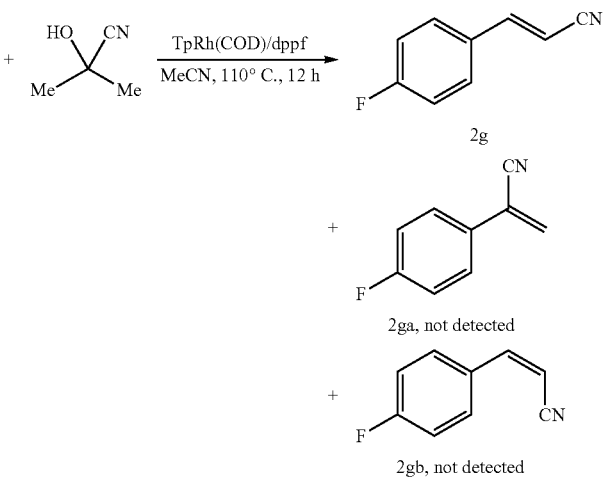

The inventors evaluated the selectivity of Markovnikov vs. anti Markovnikov addition, and Z vs. E addition selectivity by GC-MS. To establish that the inventors have chosen an appropriate method to identify the isomers, the inventors provide here a detailed analysis that unambiguously established that for compound 2g, within limits of detection, no other isomers could be detected during or after the reaction. The inventors further show that the isomers are neither destroyed during the reaction, which excludes a reaction with lower selectivity, followed by destruction of the undesired isomers.

Upon complete (>95%) conversion of alkyne 1g, product 2g was isolated in 62% yield. Independent synthesis of Markovnikov isomer 2ga (synthesis, see below) and Z isomer 2gb (synthesis, see below), allowed us to determine the content of 2ga and 2gb during hydrocyanation and after completion to form 2g. GC-MS analysis showed different retention times for all three isomers, respectively: 2g: 5.07 min; 2ga: 4.50 min; 2gb: 4.75 min. No other isomer could be identified, no other product than 2g could be identified by GC MS. GC-MS of the reaction mixture of hydrocyanation of 4-fluorophenylacetylene after 6 h showed a single product peak of the desired product.

2-(4-Fluorophenyl)acrylonitrile (2ga)

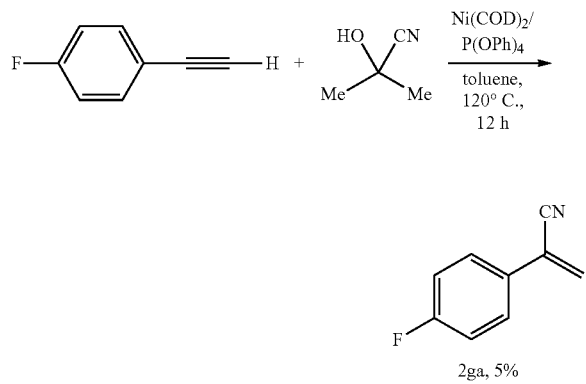

According to a literature procedure[2], in an anhydrous, argon-filled glovebox, a 20 mL vial was charged with Ni(COD)$_2$ (13.8 mg, 50.0 μmol, 5.00 mol %), P(OPh)$_4$ (80.6 mg, 100 μmol, 10.0 mol %) and toluene (10.0 mL, c=0.2 M). 4-Fluorophenylacetylene (244 mg, 2.00 mmol, 1.00 equiv.) and acetone cyanohydrin (340 mg, 380 μL, 4.00 mmol, 2.00 equiv) were then added to the reaction mixture. The vial was sealed with a Teflon cap and moved from the glovebox to a preheated metal heating block (120° C.). The reaction mixture was then stirred at 120° C. for 12 hours. After cooling to 23° C., the resulting mixture was filtered through a short plug of silica gel, eluting with EtOAc. The filtrate was collected and concentrated in vacuo. The resulting residue was purified by flash column chromatography on silica gel, eluting with EtOAc/hexane 1:20 (v/v) to afford 14.7 mg (5%) of the title compound as pale yellow crystals.

Rf=0.40 (EtOAc/hexanes 1:10 (v/v)).

NMR Spectroscopy:

$^1$H NMR (500 MHz, CDCl$_3$, 23° C., δ): 7.60-7.58 (m, 2H), 7.14-7.10 (m, 2H), 6.27 (s, 1H), 6.09 (d, J=12 Hz, 1H).

$^{13}$C NMR (125 MHz, CDCl$_3$, 23° C., δ): 156.3 (d, J=242 Hz), 128.7, 128.0 (d, J=8.5 Hz), 127.0 (d, J=2.6 Hz), 122.1, 117.6, 116.3 (d, J=22.3 Hz).

$^{19}$F NMR (471 MHz, CDCl$_3$, 23° C., δ): −110.5.

HRMS-FIA (m/z): calc'd for C$_9$H$_6$NF [M]$^+$, 147.0479; found: 147.0480.

(Z)-3-(4-Fluorophenyl)acrylonitrile (2gb)

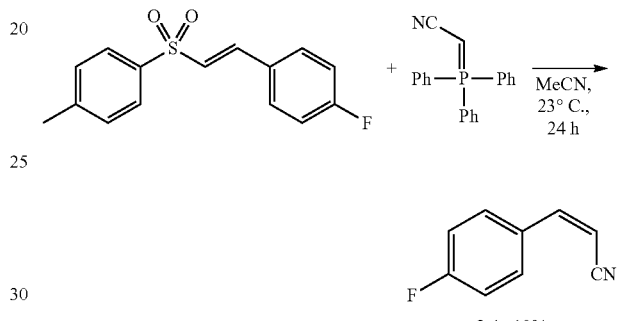

According to a literature procedure, to a solution of N-(p-tolylsulfonyl) imine (275 mg, 1.00 mmol, 1.00 equiv.) in acetonitrile (4.0 mL, c=0.25 M) under nitrogen at room temperature was added the nitrile-stabilized phosphonium ylide (361 mg, 1.20 mmol, 1.20 equiv). The mixture was stirred at room temperature for 24 h. The resulting mixture was filtered through a short plug of silica gel, eluting with EtOAc. The filtrate was collected and concentrated in vacuo. The resulting residue was purified by flash column chromatography on silica gel, eluting with EtOAc/hexane 1:20 (v/v) to afford 14.7 mg (10%) of the title compound as pale yellow crystals.

Rf=0.40 (EtOAc/hexanes 1:10 (v/v)).

NMR Spectroscopy:

$^1$H NMR (500 MHz, CDCl$_3$, 23° C., δ): 7.84-7.81 (m, 2H), 7.15-7.12 (m, 2H), 7.09 (d, J=12 Hz, 1H), 5.43 (d, J=12 Hz, 1H).

$^{13}$C NMR (125 MHz, CDCl$_3$, 23° C., δ): 164.1 (d, J=252 Hz), 147.5 (d, J=1.8 Hz), 131.3 (d, J=7.2 Hz), 130.0 (d, J=3.75 Hz), 117.4, 116.3 (d, J=21.8 Hz), 95.1 (d, J=1.75 Hz).

$^{19}$F NMR (471 MHz, CDCl$_3$, 23° C., δ): −107.7.

HRMS-FIA (m/z): calc'd for C$_9$H$_6$NF [M]$^+$, 147.0479; found: 147.0481.

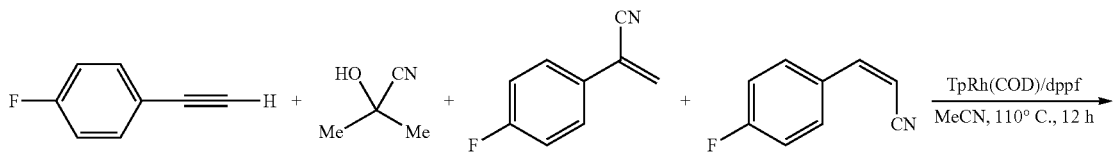

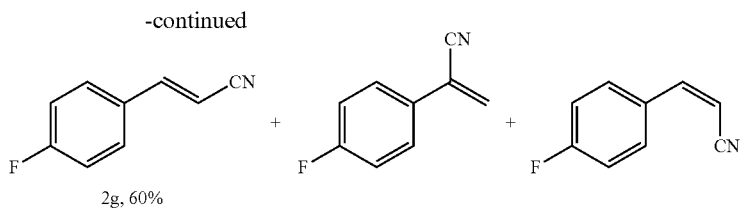

2g, 60%

GC-MS of the hydrocyanation of 4-fluorophenylacetylene with 2ga and 2gb spiking at the beginning of the reaction. The other isomers are not destroyed during the reaction.

In an anhydrous, argon-filled glovebox, a 4 mL vial was charged with TpRh(COD) (6.3 mg, 15 µmol, 7.5 mol %), dppf (8.3 mg, 15 µmol, 7.5 mol %), and MeCN (1.0 mL, c=0.2 M). 4-Fluorophenylacethlene (24.0 mg, 23.5 µL, 0.200 mmol, 1.00 equiv) and acetone cyanohydrin (17.0 mg, 19.5 µL, 0.200 mmol, 1.00 equiv), 2-(4-fluorophenyl)acrylonitrile (29.4 mg, 0.200 mmol, 1.00 equiv.) and (Z)-3-(4-fluorophenyl)acrylonitrile (14.7 mg, 0.100 mmol, 1.00 equiv.) were then added to the reaction mixture. The vial was sealed with a Teflon cap and moved from the glovebox to a preheated metal heating block (110° C.). The reaction mixture was then stirred at 110° C. for 12 hours. After cooling to 23° C., the resulting mixture was filtered through a short plug of silica gel, eluting with EtOAc. The filtrate was collected and concentrated in vacuo. The resulting residue was purified by flash column chromatography on silica gel, eluting with EtOAc/hexane 1:10 (v/v) to afford 17.6 mg (60%) title compound as colorless solid. The Markovnikov isomer 2ga and Z isomer 2gb have been found on GC-MS without obvious decomposition. 2ga (26.5 mg, 0.190 mmol) and Z isomer 2gb (14.5 mg, 0.100 mmol) were recovered by flash column chromatography on silica gel.

5.0 mol %) were added. The resulting yellow heterogeneous mixture was cooled to 0° C. in an ice-water bath and stirred at 0° C. for 30 min. Trimethylsilylacetylene (0.39 g, 0.56 mL, 4.0 mmol, 2.0 equiv) was then added within 1 min. Subsequently, the flask was moved from the ice-water bath and heated at 90° C. for 12 h. After cooling to 23° C., the volatiles were evaporated under reduced pressure. The dark oil obtained was diluted by 2.0 mL water and extracted with hexane/Et₂O 10:1 (v/v; 2×5 mL). The organic phase was collected, dried with $Na_2SO_4$ and then concentrated under reduced pressure. MeOH (2.0 mL) and $K_2CO_3$ (0.28 g, 2.0 mmol, 1.0 equiv) were added to the residue, and the resulting mixture was stirred at 23° C. for 2 h. The volatiles were then evaporated under reduced pressure, and the resulting residue was purified by flash column chromatography on silica gel, eluting with EtOAc/hexane 1:3 (v/v) to afford 154 mg (53%) title product as off-white powder.

Rf=0.25 (EtOAc/hexanes 3:1 (v/v)).

NMR Spectroscopy:

¹H NMR (500 MHz, DMSO-d₆, 23° C., δ): 8.10 (br. s, 1H), 7.93-7.91 (m, 2H), 7.60-7.59 (m, 2H), 7.52 (br. s, 1H), 4.38 (s, 1H).

¹³C NMR (125 MHz, DMSO-d₆, 23° C., δ): 167.1, 134.4, 131.6, 127.8, 124.5, 83.0, 82.7.

4-Ethynylbenzamide (1h)

(9H-Fluoren-9-yl)-methyl (4-ethynylphenyl)carbamate (1j)

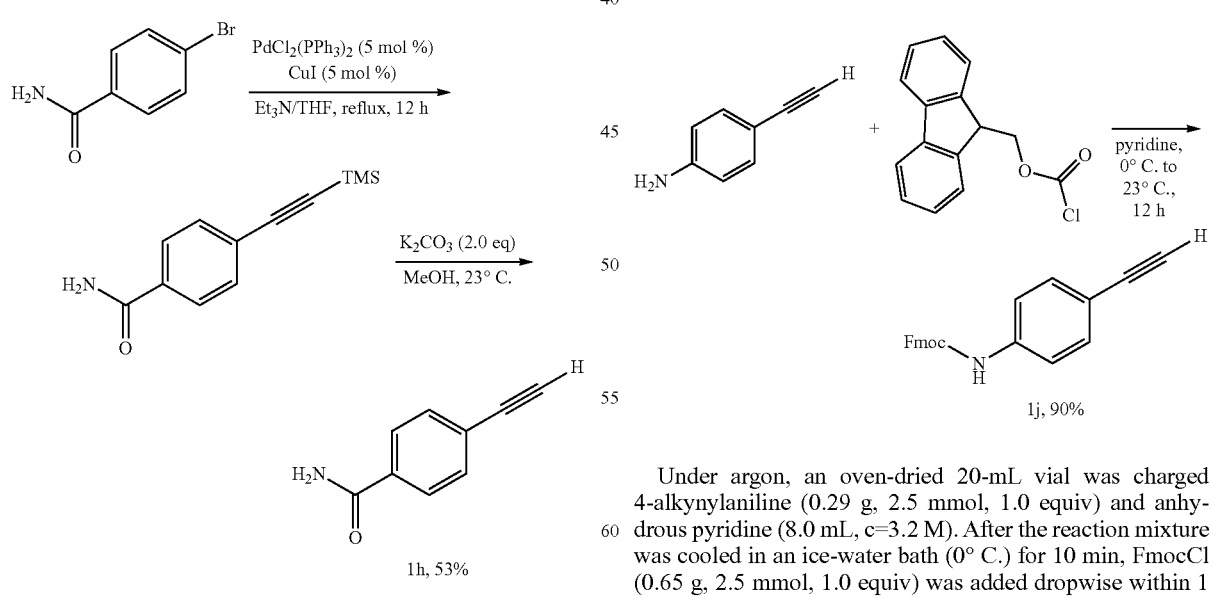

1h, 53%

1j, 90%

Under argon, an oven-dried 25-mL flask was charged with 4-bromobenzamide (0.40 g, 2.0 mmol, 1.0 equiv), Et₃N/THF (2.0 mL, 10:1 (v/v), c=1.0 M), to which PdCl₂(PPh₃)₂ (70 mg, 0.10 mmol, 5.0 mol %) and CuI (19 mg, 0.10 mmol, Under argon, an oven-dried 20-mL vial was charged 4-alkynylaniline (0.29 g, 2.5 mmol, 1.0 equiv) and anhydrous pyridine (8.0 mL, c=3.2 M). After the reaction mixture was cooled in an ice-water bath (0° C.) for 10 min, FmocCl (0.65 g, 2.5 mmol, 1.0 equiv) was added dropwise within 1 min. The reaction mixture was stirred at 0° C. for 1 h and then at 23° C. for 12 h. The resulting mixture was then acidified with HCl aqueous solution (1.5 mL, c=1.0 M) to pH around 3, and the acidified mixture was extracted with ethyl acetate (EtOAc, 20 mL). The resulting water phase was further extracted with EtOAc (2×15 mL), and the combined organic phase was subsequently washed with saturated NaHCO$_3$ aqueous solution (15 mL), followed by brine (15 mL). The organic phase was dried over anhydrous MgSO$_4$, and the solvent was then evaporated under reduced pressure to afford a brown solid. Further recrystallization from EtOAc (approximately 2.0 mL) afforded 765 mg (90%) of the title compound as yellow powder.

Rf=0.35 (EtOAc/hexanes 1:4 (v/v)).

NMR Spectroscopy:

$^1$H NMR (500 MHz, DMSO-d$_6$, 23° C., δ): 9.91 (s, 1H), 7.91 (d, J=7.5 Hz, 2H), 7.75 (d, J=7.5 Hz, 2H), 7.47-7.32 (m, 8H), 4.52 (d, J=6.5 Hz, 2H), 4.33 (t, J=6.5 Hz, 1H), 4.05 (s, 1H).

$^{13}$C NMR (125 MHz, DMSO-d$_6$, 23° C., δ): 153.7, 144.2, 141.3, 140.1, 132.9, 128.2, 127.6, 125.6, 120.7, 118.5, 115.8, 84.1, 80.1, 66.2, 47.2.

HRMS-ESI (m/z) calc'd for C$_{23}$H$_{17}$NO$_2$ [M+Na]$^+$, 362.1152, found: 362.1151.

Methyl 2-ethynylbenzoate (1l)

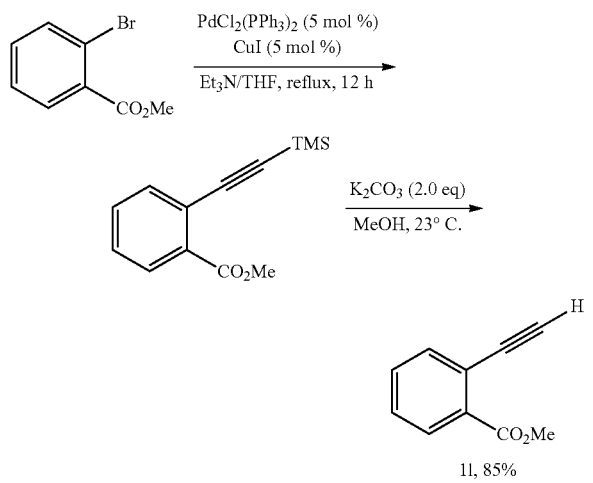

1l, 85%

Under argon, an oven-dried 25-mL flask was charged with methyl 2-bromobenzoate (0.43 g, 2.0 mmol, 1.0 equiv) and Et$_3$N/THF (2.0 mL, 10:1 (v/v), c=1.0 M), to which PdCl$_2$(PPh$_3$)$_2$ (70 mg, 0.10 mmol, 5.0 mol %) and CuI (19 mg, 0.10 mmol, 5.0 mol %) were added. The resulting yellow heterogeneous mixture was cooled to 0° C. in an ice-water bath and stirred at 0° C. for 30 min. Trimethylsilylacetylene (0.39 g, 0.56 mL, 4.0 mmol, 2.0 equiv) was then added within 1 min. Subsequently, the flask was moved from the ice-water bath and heated at 90° C. for 12 h. After cooling to 23° C., the volatiles were evaporated under reduced pressure. The dark oil obtained was diluted with 2.0 mL water, and the mixture was extracted with hexane/Et$_2$O 10:1 (v/v). The organic phase was separated, dried by Na$_2$SO$_4$ and then concentrated under reduced pressure. MeOH (2.0 mL) and K$_2$CO$_3$ (0.28 g, 2.0 mmol, 1.0 equiv) were added to the residue, and the resulting mixture was stirred at 23° C. for 2 h. The solvent was then evaporated, and the resulting residue was purified by flash column chromatography on silica gel, eluting with EtOAc/hexane 1:10 (v/v) to afford 272 mg (55%) of the title compound as yellow oil.

Rf=0.30 (EtOAc/hexanes 1:8 (v/v)).

NMR Spectroscopy:

$^1$H NMR (500 MHz, CDCl$_3$, 23° C., δ): 7.95-7.93 (m, 1H), 7.63-7.61 (m, 1H), 7.49-7.45 (m, 1H), 7.42-7.38 (m, 1H), 3.93 (s, 3H), 3.39 (s, 1H).

$^{13}$C NMR (125 MHz, CDCl$_3$, 23° C., δ): 166.6, 135.1, 132.6, 131.8, 130.4, 128.6, 122.8, 82.4, 82.1, 52.3.

HRMS-EI (m/z) calc'd for C$_{10}$H$_8$O$_2$ [M]$^+$, 160.0519, found: 160.0520.

5-Ethynyl-6-methoxy-2,3-dihydro-1H-inden-1-one (1q)

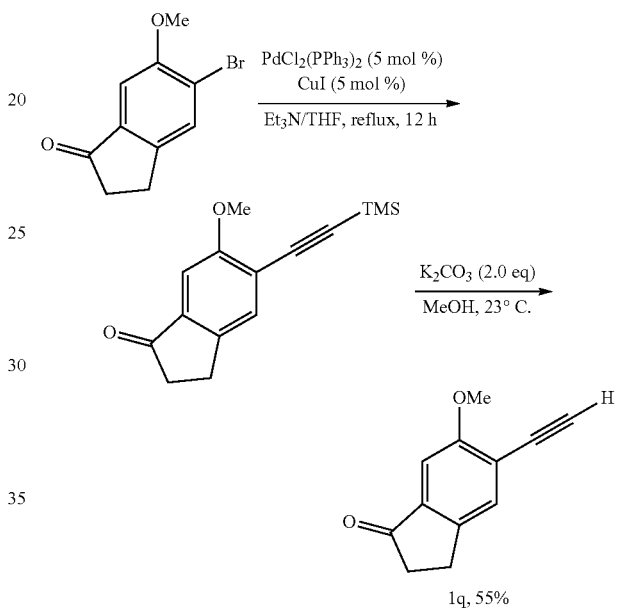

1q, 55%

Under argon, an oven-dried 25-mL flask was charged with 5-bromo-6-methoxy-2,3-dihydro-1H-inden-1-one (0.48 g, 2.0 mmol, 1.0 equiv) and Et$_3$N/THF (2.0 mL, 10:1 (v/v), c=1.0 M), to which PdCl$_2$(PPh$_3$)$_2$ (70 mg, 0.10 mmol, 5.0 mol %) and CuI (19 mg, 0.10 mmol, 5.0 mol %) were added. The resulting yellow heterogeneous mixture was cooled to 0° C. in an ice-water bath and stirred at 0° C. for 30 min. Trimethylsilylacetylene (0.39 g, 0.56 mL, 4.0 mmol, 2.0 equiv) was then added within 1 min. Subsequently, the flask was moved from the ice-water bath and heated at 90° C. for 12 h. After cooling to 23° C., the volatiles were evaporated under reduced pressure. The dark oil obtained was diluted with 2.0 mL water, and the mixture extracted with hexane-Et$_2$O 10:1 (v/v). The organic phase was separated, dried by Na$_2$SO$_4$ and then concentrated under reduced pressure. MeOH (2.0 mL) and K$_2$CO$_3$ (0.28 g, 2.0 mmol, 1.0 equiv) were added to the residue, and the resulting mixture was stirred at 23° C. for 2 h. The solvent was then evaporated, and the resulting residue was purified by flash column chromatography on silica gel, eluting with EtOAc/hexane 6:1 (v/v) to afford 205 mg (55%) of the title compound as colorless oil.

Rf=0.30 (EtOAc/hexanes 1:4 (v/v)).

NMR Spectroscopy:

$^1$H NMR (500 MHz, CDCl$_3$, 23° C., δ): 7.48 (s, 1H), 7.11 (s, 1H), 3.85 (s, 3H), 3.42 (s, 1H), 2.98 (t, J=5.5 Hz, 2H), 2.64 (t, J=5.5 Hz, 2H).

$^{13}$C NMR (125 MHz, CDCl$_3$, 23° C., δ): 206.3, 160.2, 146.8, 138.2, 131.9, 118.5, 103.9, 84.5, 79.6, 56.2, 36.9, 24.8.

HRMS-EI (m/z) calc'd for C$_{12}$H$_{10}$O$_2$ [M]$^+$, 186.0676, found: 186.0675.

2-Ethoxy-5-ethynylpyridine (1u)

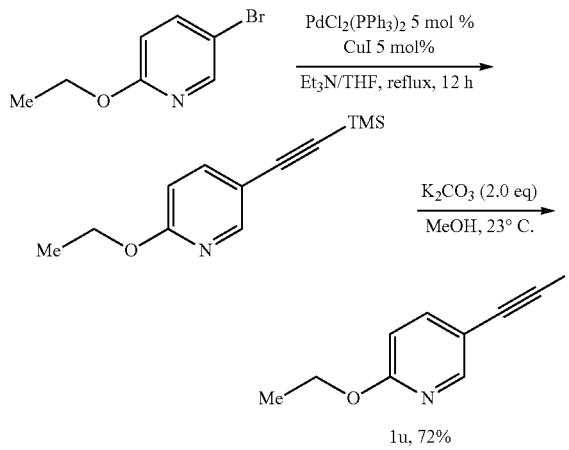

1u, 72%

Under argon, an oven-dried 25-mL flask was charged with 5-bromo-2-ethoxypyridine (0.40 g, 2.0 mmol, 1.0 equiv) and Et$_3$N/THF (2.0 mL, 10:1 (v/v), c=1.0 M), to which PdCl$_2$(PPh$_3$)$_2$ (70 mg, 0.10 mmol, 5.0 mol %) and CuI (19 mg, 0.10 mmol, 5.0 mol %) were added. The resulting yellow heterogeneous mixture was cooled to 0° C. in an ice-water bath and stirred at 0° C. for 30 min. Trimethylsilylacetylene (0.39 g, 0.56 mL, 4.0 mmol, 2.0 equiv) was then added within 1 min. Subsequently, the flask was moved from the ice-water bath and heated at 90° C. for 12 h. After cooling to 23° C., the volatiles were evaporated under reduced pressure. The dark oil obtained was diluted by 2.0 mL water, and the mixture extracted with hexane/Et$_2$O 10:1 (v/v). The organic phase was separated, dried by Na$_2$SO$_4$ and then concentrated under reduced pressure. MeOH (2.0 mL) and K$_2$CO$_3$ (0.28 g, 2.0 mmol, 1.0 equiv) were added to the residue and the resulting mixture was stirred at 23° C. for 2 h. The solvent was then evaporated and the resulting residue was purified by flash column chromatography on silica gel, eluting with EtOAc/hexane 10:1 (v/v) to afford 212 mg (72%) of the title compound as colorless oil.

Rf=0.25 (EtOAc/hexanes 1:9 (v/v)).

NMR Spectroscopy:

$^1$H NMR (500 MHz, CDCl$_3$, 23° C., δ): 8.28 (s, 1H), 7.26 (s, 1H), 6.66 (d, J=8.6 Hz, 1H), 4.36 (q, J=7.0 Hz, 2H), 3.09 (s, 1H), 1.38 (t, J=7.0 Hz, 3H).

$^{13}$C NMR (125 MHz, CDCl$_3$, 23° C., δ): 163.4, 150.8, 141.5, 111.8, 110.8, 80.8, 78.5, 62.1, 14.6.

HRMS-EI (m/z) calc'd for C$_9$H$_9$NO [M]$^+$, 147.0679, found: 147.0680.

Cinnamonitrile (2a)

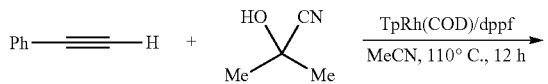

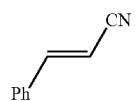

2a, 88%

In an anhydrous, argon-filled glovebox, a 4 mL vial was charged with TpRh(COD) (6.3 mg, 15 μmol, 7.5 mol %), dppf (8.3 mg, 15 μmol, 7.5 mol %), and MeCN (1.0 mL, c=0.2 M). Phenylacetylene (20.4 mg, 22.0 μL, 0.200 mmol, 1.00 equiv) and and acetone cyanohydrin (17.0 mg, 19.5 μL, 0.200 mmol, 1.00 equiv) were then added to the reaction mixture. The vial was sealed with a Teflon cap and moved from the glovebox to a preheated metal heating block (110° C.). The reaction mixture was then stirred at 110° C. for 12 hours. After cooling to 23° C., the resulting mixture was filtered through a short plug of silica gel, eluting with EtOAc. The filtrate was collected and concentrated in vacuo. The resulting residue was purified by flash column chromatography on silica gel, eluting with EtOAc/hexane 1:10 (v/v) to afford 22.7 mg (88%) of the title compound as pale yellow oil.

Rf=0.45 (EtOAc/hexanes 1:10 (v/v)).

NMR Spectroscopy:

$^1$H NMR (500 MHz, CDCl$_3$, 23° C., δ): 7.45-7.40 (m, 5H), 7.38 (d, J=16.5 Hz, 1H), 5.87 (d, J=16.5 Hz, 1H).

$^{13}$C NMR (125 MHz, CDCl$_3$, 23° C., δ): 150.6, 133.5, 131.2, 129.1, 127.4, 118.2, 96.3.

HRMS-FIA (m/z): calc'd for C$_9$H$_7$N [M+Na]$^+$, 152.0471, found: 152.0472.

(E)-3-(4-Methoxyphenyl)acrylonitrile (2b)

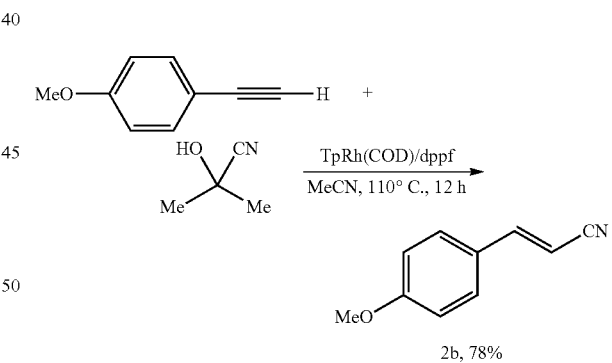

2b, 78%

In an anhydrous, argon-filled glovebox, a 4 mL vial was charged with TpRh(COD) (6.3 mg, 15 μmol, 7.5 mol %), dppf (8.3 mg, 15 μmol, 7.5 mol %), and MeCN (1.0 mL, c=0.2 M). 1-Ethynyl-4-methoxybenzene (26.4 mg, 0.200 mmol, 1.00 equiv) and acetone cyanohydrin (17.0 mg, 19.5 μL, 0.200 mmol, 1.00 equiv) were then added to the reaction mixture. The vial was sealed with a Teflon cap and moved from the glovebox to a preheated metal heating block (110° C.). The reaction mixture was then stirred at 110° C. for 12 hours. After cooling to 23° C., the resulting mixture was filtered through a short plug of silica gel, eluting with EtOAc. The filtrate was collected and concentrated in vacuo.

The resulting residue was purified by flash column chromatography on silica gel, eluting with EtOAc/hexane 1:9 (v/v) to afford 24.8 mg (78%) of the title compound as pale yellow oil.

Rf=0.45 (EtOAc/hexanes 1:19 (v/v)).

NMR Spectroscopy:

$^1$H NMR (500 MHz, CDCl$_3$, 23° C., δ): 7.39 (d, J=8.5 Hz, 2H), 7.33 (d, J=16.5 Hz, 1H), 6.91 (d, J=8.5 Hz, 2H), 5.71 (d, J=16.5 Hz, 1H), 3.85 (s, 3H).

$^{13}$C NMR (125 MHz, CDCl$_3$, 23° C., δ): 162.2, 150.2, 129.2, 126.5, 118.9, 114.7, 93.5, 55.6.

HRMS-FIA (m/z): calc'd for C$_{10}$H$_9$NO [M]$^+$, 159.0679; found: 159.0679.

(E)-3-([1,1'-Biphenyl]-4-yl)acrylonitrile (2c)

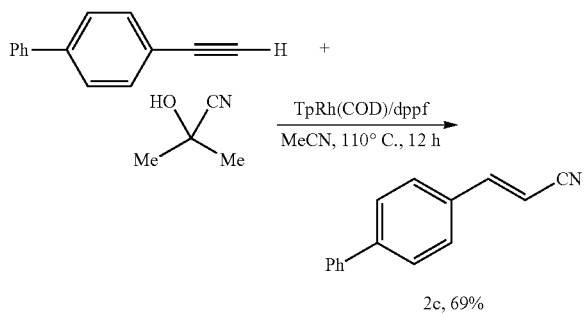

2c, 69%

In an anhydrous, argon-filled glovebox, a 4 mL vial was charged with TpRh(COD) (6.3 mg, 15 μmol, 7.5 mol %), dppf (8.3 mg, 15 μmol, 7.5 mol %), and MeCN (1.5 mL, c=0.13 M). 4-Ethynyl-1,1'-biphenyl (35.8 mg, 0.200 mmol, 1.00 equiv) and acetone cyanohydrin (20.4 mg, 23.5 μL, 0.240 mmol, 1.20 equiv) were then added to the reaction mixture. The vial was sealed with a Teflon cap and moved from the glovebox to a preheated metal heating block (110° C.). The reaction mixture was then stirred at 110° C. for 12 hours. After cooling to 23° C., the resulting mixture was filtered through a short plug of silica gel, eluting with EtOAc. The filtrate was collected and concentrated in vacuo. The resulting residue was purified by flash column chromatography on silica gel, eluting with EtOAc/hexane 1:10 (v/v) to afford 28.3 mg (69%) of the title compound as yellow solid.

Rf=0.40 (EtOAc/hexanes 1:10 (v/v)).

NMR Spectroscopy:

$^1$H NMR (500 MHz, CDCl$_3$, 23° C., δ): 7.65-7.60 (m, 4H), 7.54-7.52 (m, 2H), 7.48-7.46 (m, 2H), 7.44 (d, J=16.5 Hz, 1H), 7.41-7.38 (m, 1H), 5.91 (d, J=16.5 Hz, 1H).

$^{13}$C NMR (125 MHz, CDCl$_3$, 23° C., δ): 150.2, 144.2, 139.9, 132.6, 129.1, 128.3, 128.0, 127.9, 127.2, 118.4, 96.2.

HRMS-FIA (m/z): calc'd for C$_{15}$H$_{11}$N [M]$^+$, 205.0888; found: 205.0886.

(E)-3-(4-(tert-Butyl)phenyl)acrylonitrile (2d)

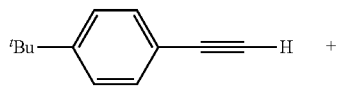

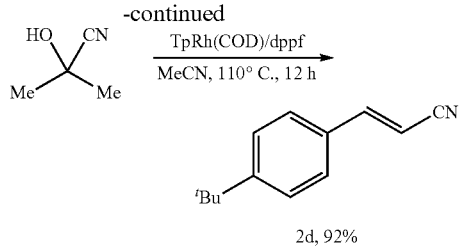

2d, 92%

In an anhydrous, argon-filled glovebox, a 4 mL vial was charged with TpRh(COD) (6.3 mg, 15 μmol, 7.5 mol %), dppf (8.3 mg, 15 μmol, 7.5 mol %), and MeCN (1.0 mL, c=0.2 M). 1-(tert-Butyl)-4-ethynylbenzene (31.6 mg, 26.5 μL, 0.200 mmol, 1.00 equiv) and acetone cyanohydrin (17.0 mg, 19.5 μL, 0.200 mmol, 1.00 equiv) were then added to the reaction mixture. The vial was sealed with a Teflon cap and moved from the glovebox to a preheated metal heating block (110° C.). The reaction mixture was then stirred at 110° C. for 12 hours. After cooling to 23° C., the resulting mixture was filtered through a short plug of silica gel, eluting with EtOAc. The filtrate was collected and concentrated in vacuo. The resulting residue was purified by flash column chromatography on silica gel, eluting with EtOAc/hexane 1:10 (v/v) to afford 34.0 mg (92%) of the title compound as pale yellow liquid.

Rf=0.45 (EtOAc/hexanes 1:10 (v/v)).

NMR Spectroscopy:

$^1$H NMR (500 MHz, CDCl$_3$, 23° C., δ): 7.44-7.37 (m, 5H), 5.84 (d, J=16.5 Hz, 1H), 1.33 (s, 9H).

$^{13}$C NMR (125 MHz, CDCl$_3$, 23° C., δ): 155.1, 150.6, 131.0, 127.4, 126.2, 118.6, 95.4, 35.1, 31.2.

HRMS-FIA (m/z): calc'd for C$_{13}$H$_{15}$N [M]$^+$, 185.1199; found: 185.1199.

Gram-Scale Synthesis of 2d

Under Ar atmosphere, an oven-dried 250 mL Schlenk flask was charged with TpRh(COD) (273 mg, 0.650 mmol, 5.00 mol %), dppf (360 mg, 0.650 mmol, 5.00 mol %), and MeCN (50 mL, c=0.26 M) 1-(tert-Butyl)-4-ethynylbenzene (2.05 g, 13.0 mmol, 1.00 equiv) and acetone cyanohydrin (1.10 g, 1.27 mL, 13.0 mmol, 1.00 equiv) were then added to the reaction mixture. The flask was sealed and moved to a preheated oil bath (110° C.). The reaction mixture was then stirred at 110° C. for 12 hours. After cooling to 23° C., the resulting mixture was filtered through a short plug of silica gel, eluting with EtOAc. The filtrate was collected and concentrated in vacuo. The resulting residue was purified by flash column chromatography on silica gel to afford 1.6 g (67%) of the title compound as pale yellow liquid.

(E)-3-(4-(Trimethylsilyl)phenyl)acrylonitrile (2e)

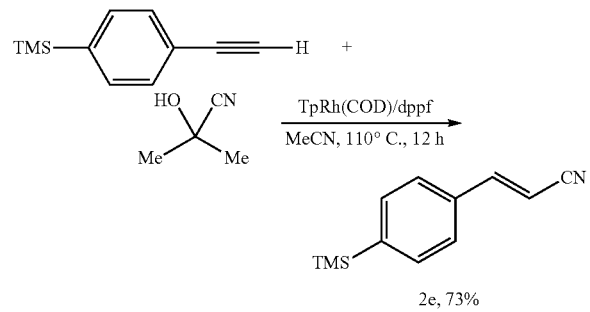

2e, 73%

In an anhydrous, argon-filled glovebox, a 4 mL vial was charged with TpRh(COD) (6.3 mg, 15 µmol, 7.5 mol %), dppf (8.3 mg, 15 µmol, 7.5 mol %), and MeCN (1.0 mL, c=0.2 M). (4-Ethynylphenyl)trimethylsilane (34.8 mg, 28.0 µL, 0.200 mmol, 1.00 equiv) and acetone cyanohydrin (20.4 mg, 23.5 µL, 0.240 mmol, 1.20 equiv) were then added to the reaction mixture. The vial was sealed with a Teflon cap and moved from the glovebox to a preheated metal heating block (110° C.). The reaction mixture was then stirred at 110° C. for 12 hours. After cooling to 23° C., the resulting mixture was filtered through a short plug of silica gel, eluting with EtOAc. The filtrate was collected and concentrated in vacuo. The resulting residue was purified by flash column chromatography on silica gel, eluting with EtOAc/hexane 1:10 (v/v) to afford 29.3 mg (73%) of the title compound as pale yellow liquid.

Rf=0.50 (EtOAc/hexanes 1:10 (v/v)).

NMR Spectroscopy:

$^1$H NMR (500 MHz, CDCl$_3$, 23° C., δ): 7.57-7.54 (m, 2H), 7.43-7.38 (m, 3H), 5.91 (d, J=16.5 Hz, 1H), 0.29 (s, 9H).

$^{13}$C NMR (125 MHz, CDCl$_3$, 23° C., δ): 150.8, 145.2, 134.2, 133.9, 126.6, 118.4, 96.5, −1.2.

HRMS-FIA (m/z): calc'd for C$_{12}$H$_{15}$NSi [M]$^+$, 201.0967; found: 201.0968.

(E)-3-(4-(4,4,5,5-Tetramethyl-1,3,2-dioxaborolan-2-yl)phenyl)acrylonitrile (2f)

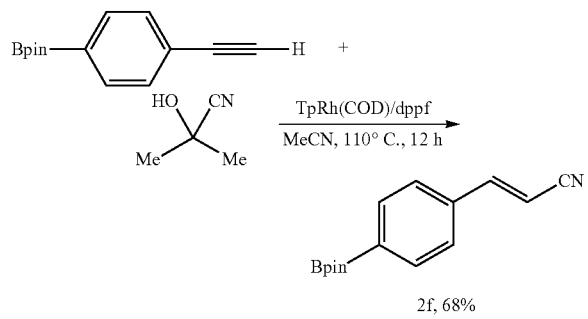

2f, 68%

In an anhydrous, argon-filled glovebox, a 4 mL vial was charged with TpRh(COD) (6.3 mg, 15 µmol, 7.5 mol %), dppf (8.3 mg, 15 µmol, 7.5 mol %), and MeCN (1.0 mL, c=0.2 M). 2-(4-Ethynylphenyl)-4,4,5,5-tetramethyl-1,3,2-dioxaborolane (45.6 mg, 0.200 mmol, 1.00 equiv) and acetone cyanohydrin (20.4 mg, 23.5 µL, 0.240 mmol, 1.20 equiv) were then added to the reaction mixture. The vial was sealed with a Teflon cap and moved from the glovebox to a preheated metal heating block (110° C.). The reaction mixture was then stirred at 110° C. for 12 hours. After cooling to 23° C., the resulting mixture was filtered through a short plug of silica gel, eluting with EtOAc. The filtrate was collected and concentrated in vacuo. The resulting residue was purified by flash column chromatography on silica gel, eluting with EtOAc/hexane 1:10 (v/v) to afford 34.7 mg (68%) of the title compound as pale yellow liquid.

Rf=0.35 (EtOAc/hexanes 1:10 (v/v)).

NMR Spectroscopy:

$^1$H NMR (500 MHz, CDCl$_3$, 23° C., δ): 7.85 (d, J=8.0 Hz, 2H), 7.46 (d, J=8.0 Hz, 2H), 7.43 (d, J=16.5 Hz, 1H), 5.96 (d, J=16.5 Hz, 1H), 1.37 (s, 12H).

$^{13}$C NMR (125 MHz, CDCl$_3$, 23° C., δ): 150.5, 135.8, 135.4, 126.5, 118.1, 97.2, 84.2, 24.9.

HRMS-FIA (m/z) calc'd for C$_{15}$H$_{18}$NO$_2$ [M+Na]$^+$, 278.1323; found: 278.1324.

(E)-3-(4-Fluorophenyl)acrylonitrile (2q)

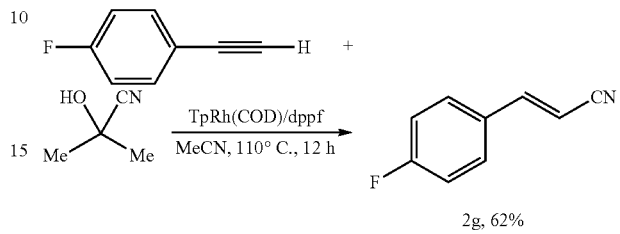

2g, 62%

In an anhydrous, argon-filled glovebox, a 4 mL vial was charged with TpRh(COD) (6.3 mg, 15 µmol, 7.5 mol %), dppf (8.3 mg, 15 µmol, 7.5 mol %), and MeCN (1.0 mL, c=0.2 M). 4-Fluorophenylacetylene (24.0 mg, 23.5 µL, 0.200 mmol, 1.00 equiv) and acetone cyanohydrin (17.0 mg, 19.5 µL, 0.200 mmol, 1.00 equiv) were then added to the reaction mixture. The vial was sealed with a Teflon cap and moved from the glovebox to a preheated metal heating block (110° C.). The reaction mixture was then stirred at 110° C. for 12 hours. After cooling to 23° C., the resulting mixture was filtered through a short plug of silica gel, eluting with EtOAc. The filtrate was collected and concentrated in vacuo. The resulting residue was purified by flash column chromatography on silica gel, eluting with EtOAc/hexane 1:10 (v/v) to afford 18.2 mg (62%) of the title compound as colorless solid.

Rf=0.45 (EtOAc/hexanes 1:10 (v/v)).

NMR Spectroscopy:

$^1$H NMR (500 MHz, CDCl$_3$, 23° C., δ): 7.47-7.44 (m, 2H), 7.36 (d, J=16.5 Hz, 1H), 7.12-7.09 (m, 2H), 5.81 (d, J=16.5 Hz, 1H).

$^{13}$C NMR (125 MHz, CDCl$_3$, 23° C., δ): 164.6 (d, J=253.5 Hz), 149.4, 129.9 (d, J=3.1 Hz), 129.5 (d, J=8.8 Hz), 118.1, 116.5 (d, J=22.0 Hz), 96.3.

$^{19}$F NMR (471 MHz, CDCl$_3$, 23° C., δ): −107.8.

HRMS-FIA (m/z): calc'd for C$_9$H$_6$NF [M]$^+$, 147.0479; found: 147.0481.

(E)-4-(2-Cyanovinyl)benzamide (2h)

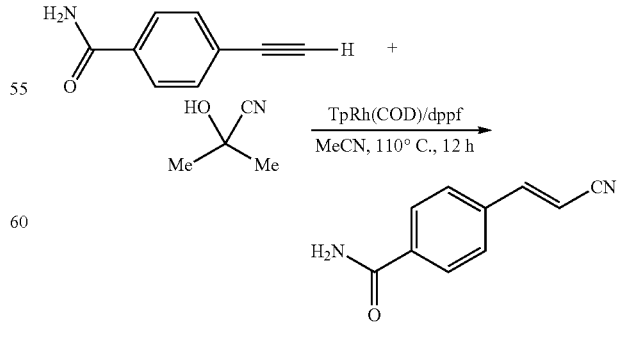

2h, 51%

In an anhydrous, argon-filled glovebox, a 4 mL vial was charged with TpRh(COD) (6.3 mg, 15 µmol, 7.5 mol %), dppf (8.3 mg, 15 µmol, 7.5 mol %), and MeCN (1.5 mL, c=0.13 M). 4-Ethynylbenzamide (29.0 mg, 0.200 mmol, 1.00 equiv) and acetone cyanohydrin (17.0 mg, 19.5 µL, 0.200 mmol, 1.00 equiv) were then added to the reaction mixture. The vial was sealed with a Teflon cap and moved from the glovebox to a preheated metal heating block (110° C.). The reaction mixture was then stirred at 110° C. for 12 hours. After cooling to 23° C., the resulting mixture was filtered through a short plug of silica gel, eluting with EtOAc. The filtrate was collected and concentrated in vacuo. The resulting residue was purified by flash column chromatography on silica gel, eluting with EtOAc/hexane 2:1 (v/v) to afford 17.5 mg (51%) of the title compound as colorless solid.

Rf=0.25 (EtOAc/hexanes 2:1 (v/v)).

NMR Spectroscopy:

$^1$H NMR (500 MHz, DMSO-$d_6$, 23° C., δ): 8.05 (br. s, 1H), 7.92-7.89 (m, 2H), 7.74-7.69 (m, 3H), 7.49-7.47 (br. m, 1H), 6.58 (d, J=16.5 Hz, 1H).

$^{13}$C NMR (125 MHz, DMSO-$d_6$, 23° C., δ): 167.5, 150.1, 136.7, 128.5, 128.1, 127.2, 119.1, 98.9.

HRMS-FIA (m/z) calc'd for $C_{10}H_7N_2O$ [M−H]$^-$, 171.0564; found: 171.0564.

(E)-4-(2-Cyanovinyl)benzonitrile (2i)

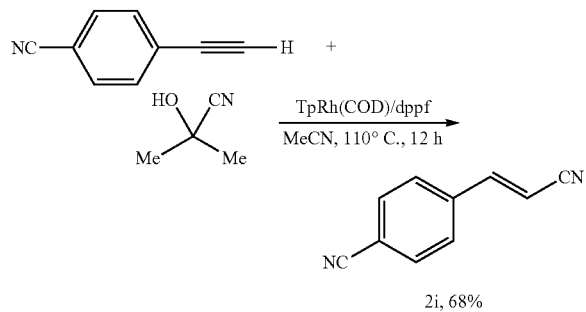

2i, 68%

In an anhydrous, argon-filled glovebox, a 4 mL vial was charged with TpRh(COD) (6.3 mg, 15 µmol, 7.5 mol %), dppf (8.3 mg, 15 µmol, 7.5 mol %), and MeCN (1.0 mL, c=0.2 M). 4-Ethynylbenzonitrile (25.4 mg, 0.200 mmol, 1.00 equiv) and acetone cyanohydrin (17.0 mg, 19.5 µL, 0.200 mmol, 1.00 equiv) were then added to the reaction mixture. The vial was sealed with a Teflon cap and moved from the glovebox to a preheated metal heating block (110° C.). The reaction mixture was then stirred at 110° C. for 12 hours. After cooling to 23° C., the resulting mixture was filtered through a short plug of silica gel, eluting with EtOAc. The filtrate was collected and concentrated in vacuo. The resulting residue was purified by flash column chromatography on silica gel, eluting with EtOAc/hexane 1:9 (v/v) to afford 20.9 mg (68%) of the title compound as yellow solid.

Rf=0.35 (EtOAc/hexanes 1:9 (v/v)).

NMR Spectroscopy:

$^1$H NMR (500 MHz, CDCl$_3$, 23° C., δ): 7.72-7.70 (m, 2H), 7.57-7.55 (m, 2H), 7.42 (d, J=16.5 Hz, 1H), 6.00 (d, J=16.5 Hz, 1H).

$^{13}$C NMR (125 MHz, CDCl$_3$, 23° C., δ): 148.2, 137.5, 132.7, 127.8, 118.0, 117.1, 114.5, 100.3.

HRMS-FIA (m/z) calc'd for $C_{10}H_6N_2$ [M]$^+$, 154.0525; found: 154.0525.

(9H-Fluoren-9-yl)methyl (E)-(4-(2-cyanovinyl)phenyl)carbamate (2i)

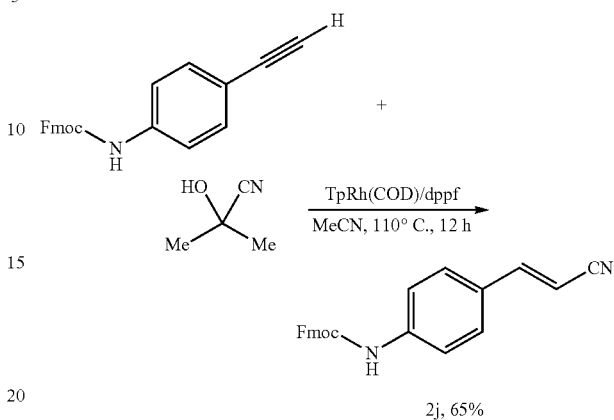

2j, 65%

In an anhydrous, argon-filled glovebox, a 4 mL vial was charged with TpRh(COD) (6.3 mg, 15 µmol, 7.5 mol %), dppf (8.3 mg, 15 µmol, 7.5 mol %), and MeCN (1.5 mL, c=0.13 M). (9H-Fluoren-9-yl)methyl (4-ethynylphenyl)carbamate (67.8 mg, 0.200 mmol, 1.00 equiv) and acetone cyanohydrin (17.0 mg, 19.5 µL, 0.200 mmol, 1.00 equiv) were then added to the reaction mixture. The vial was sealed with a Teflon cap and moved from the glovebox to a preheated metal heating block (110° C.). The reaction mixture was then stirred at 110° C. for 12 hours. After cooling to 23° C., the resulting mixture was filtered through a short plug of silica gel, eluting with EtOAc. The filtrate was collected and concentrated in vacuo. The resulting residue was purified by flash column chromatography on silica gel, eluting with EtOAc/hexane 1:4 (v/v) to afford 47.6 mg (65%) of the title compound as pale yellow solid.

Rf=0.35 (EtOAc/hexanes 1:4 (v/v)).

NMR Spectroscopy:

$^1$H NMR (500 MHz, DMSO-$d_6$, 23° C., δ): 10.02 (br. s, 1H), 7.91 (d, J=7.5 Hz, 2H), 7.75 (d, J=7.5 Hz, 2H), 7.59-7.53 (m, 5H), 7.43 (dd, J=7.5 Hz, 7.5 Hz, 2H), 7.36 (dd, J=7.5 Hz, 7.5 Hz, 2H), 6.29 (d, J=16.5 Hz, 1H), 4.53 (d, J=6.0 Hz, 2H), 4.32 (t, J=6.0 Hz, 1H).

$^{13}$C NMR (125 MHz, DMSO-$d_6$, 23° C., δ): 153.2, 150.1, 143.7, 141.7, 140.8, 128.7, 128.0, 127.1, 125.1, 120.2, 119.2, 118.1, 94.3.

HRMS-FIA (m/z) calc'd for $C_{24}H_{18}N_2O_2Na$ [M+Na]$^+$, 389.1259; found: 389.1260.

Note: 17% (11.5 mg) of alkyne were recovered by flash column chromatography.

(E)-3-(o-Tolyl)acrylonitrile (2k)

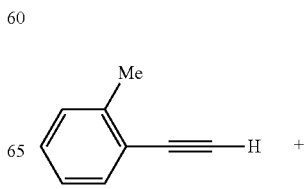

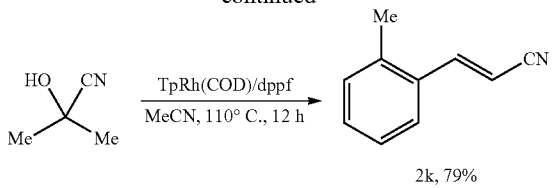

In an anhydrous, argon-filled glovebox, a 4 mL vial was charged with TpRh(COD) (6.3 mg, 15 μmol, 7.5 mol %), dppf (8.3 mg, 15 μmol, 7.5 mol %), and MeCN (1.0 mL, c=0.2 M). 1-Ethynyl-2-methylbenzene (23.2 mg, 21.2 μL, 0.200 mmol, 1.00 equiv) and acetone cyanohydrin (17.0 mg, 19.5 μL, 0.200 mmol, 1.00 equiv) were then added to the reaction mixture. The vial was sealed with a Teflon cap and moved from the glovebox to a preheated metal heating block (110° C.). The reaction mixture was then stirred at 110° C. for 12 hours. After cooling to 23° C., the resulting mixture was filtered through a short plug of silica gel, eluting with EtOAc. The filtrate was collected and concentrated in vacuo. The resulting residue was purified by flash column chromatography on silica gel, eluting with EtOAc/hexane 1:10 (v/v) to afford 22.6 mg (79%) of the title compound as pale yellow liquid.

Rf=0.45 (EtOAc/hexanes 1:10 (v/v)).
NMR Spectroscopy:
$^1$H NMR (500 MHz, CDCl$_3$, 23° C., δ): 7.70 (d, J=16.5 Hz, 1H), 7.46 (d, J=7.4 Hz, 1H), 7.33 (dd, J=8.1, 7.4 Hz, 1H), 7.23 (dd, J=7.7, 7.4 Hz, 2H), 5.80 (d, J=16.5 Hz, 1H), 2.41 (s, 3H).
$^{13}$C NMR (125 MHz, CDCl$_3$, 23° C., δ): 148.4, 137.2, 132.5, 131.0, 130.9, 126.6, 125.5, 118.3, 97.2, 19.6.
HRMS-FIA (m/z) calc'd for C$_{10}$H$_9$N [M]$^+$, 143.0732; found: 143.0729.

Methyl (E)-2-(2-cyanovinyl)benzoate (2l)

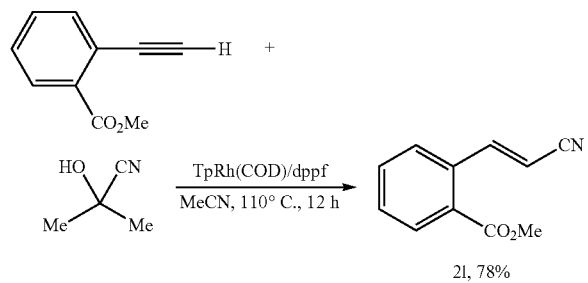

In an anhydrous, argon-filled glovebox, a 4 mL vial was charged with TpRh(COD) (6.3 mg, 15 μmol, 7.5 mol %), dppf (8.3 mg, 15 μmol, 7.5 mol %), and MeCN (1.0 mL, c=0.2 M). Methyl 2-ethynylbenzoate (32.0 mg, 0.200 mmol, 1.00 equiv) and acetone cyanohydrin (17.0 mg, 19.5 μL, 0.200 mmol, 1.00 equiv) were then added to the reaction mixture. The vial was sealed with a Teflon cap and moved from the glovebox to a preheated metal heating block (110° C.). The reaction mixture was then stirred at 110° C. for 12 hours. After cooling to 23° C., the resulting mixture was filtered through a short plug of silica gel, eluting with EtOAc. The filtrate was collected and concentrated in vacuo. The resulting residue was purified by flash column chromatography on silica gel, eluting with EtOAc/hexane 1:6 (v/v) to afford 29.1 mg (78%) of the title compound as yellow solid.

Rf=0.40 (EtOAc/hexanes 1:6 (v/v)).
NMR Spectroscopy:
$^1$H NMR (500 MHz, CDCl$_3$, 23° C., δ): 8.31 (d, J=16.5 Hz, 1H), 8.01 (dd, J=7.5, 1.5 Hz, 1H), 7.57-7.49 (m, 3H), 5.77 (d, J=16.5 Hz, 1H), 3.94 (s, 3H).
$^{13}$C NMR (125 MHz, CDCl$_3$, 23° C., δ): 166.8, 150.2, 135.5, 132.8, 131.3, 130.4, 129.3, 127.4, 117.9, 99.2, 52.7.
HRMS-FIA (m/z) calc'd for C$_{11}$H$_9$NO$_2$ [M]$^+$, 187.0627; found: 187.0628.

(E)-3-(2-Chlorophenyl)acrylonitrile (2m)

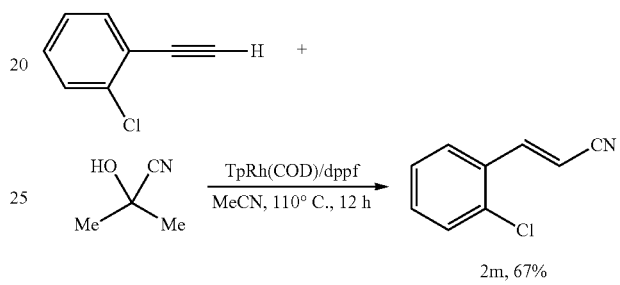

In an anhydrous, argon-filled glovebox, a 4 mL vial was charged with TpRh(COD) (6.3 mg, 15 μmol, 7.5 mol %), dppf (8.3 mg, 15 μmol, 7.5 mol %), and MeCN (1.0 mL, c=0.2 M). 1-Chloro-2-ethynylbenzene (27.2 mg, 0.200 mmol, 1.00 equiv) and acetone cyanohydrin (17.0 mg, 19.5 μL, 0.200 mmol, 1.00 equiv) were then added to the reaction mixture. The vial was sealed with a Teflon cap and moved from the glovebox to a preheated metal heating block (110° C.). The reaction mixture was then stirred at 110° C. for 12 hours. After cooling to 23° C., the resulting mixture was filtered through a short plug of silica gel, eluting with EtOAc. The filtrate was collected and concentrated in vacuo. The resulting residue was purified by flash column chromatography on silica gel, eluting with EtOAc/hexane 1:10 (v/v) to afford 21.8 mg (67%) of the title compound as yellow solid.

Rf=0.40 (EtOAc/hexanes 1:10 (v/v)).
NMR Spectroscopy:
$^1$H NMR (500 MHz, CDCl$_3$, 23° C., δ): 7.84 (d, J=16.5 Hz, 1H), 7.54 (dd, J=8.0, 1.5 Hz, 1H), 7.44 (dd, J=8.0, 1.5 Hz, 1H), 7.37 (ddd, J=7.6, 7.4, 1.5 Hz, 1H), 7.31 (ddd, J=7.6, 7.4, 1.5 Hz, 1H), 5.91 (d, J=16.5 Hz, 1H).
$^{13}$C NMR (125 MHz, CDCl$_3$, 23° C., δ): 146.6, 134.5, 132.0, 131.8, 130.4, 127.3, 126.9, 117.7, 98.9.
HRMS-FIA (m/z) calc'd for C$_9$H$_6$NCl [M]$^+$, 163.0182; found: 163.0183.

(E)-3-(2-(Hydroxymethyl)phenyl)acrylonitrile (2n)

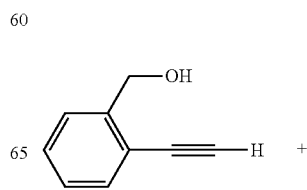

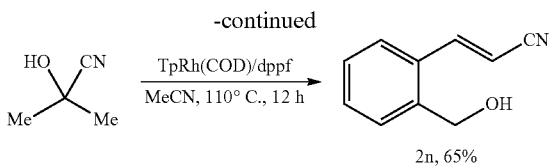

2n, 65%

In an anhydrous, argon-filled glovebox, a 4 mL vial was charged with TpRh(COD) (6.3 mg, 15 μmol, 7.5 mol %), dppf (8.3 mg, 15 μmol, 7.5 mol %), and MeCN (1.0 mL, c=0.2 M). (2-Ethynylphenyl)methanol (26.4 mg, 0.200 mmol, 1.00 equiv) and acetone cyanohydrin (17.0 mg, 19.5 μL, 0.200 mmol, 1.00 equiv) were then added to the reaction mixture. The vial was sealed with a Teflon cap and moved from the glovebox to a preheated metal heating block (110° C.). The reaction mixture was then stirred at 110° C. for 12 hours. After cooling to 23° C., the resulting mixture was filtered through a short plug of silica gel, eluting with EtOAc. The filtrate was collected and concentrated in vacuo. The resulting residue was purified by flash column chromatography on silica gel, eluting with EtOAc/hexane 1:4 (v/v) to afford 20.7 mg (65%) of the title compound as pale yellow liquid.

Rf=0.25 (EtOAc/hexanes 1:4 (v/v)).

NMR Spectroscopy:

$^1$H NMR (500 MHz, CDCl$_3$, 23° C., δ): 7.75 (d, J=16.5 Hz, 1H), 7.44 (d, J=7.6 Hz, 1H), 7.36-7.32 (m, 2H) 7.28 (m, 1H), 5.80 (d, J=16.5 Hz, 1H), 4.65 (s, 2H), 2.21 (s, 1H).

$^{13}$C NMR (125 MHz, CDCl$_3$, 23° C., δ): 148.1, 139.0, 132.6, 131.1, 129.3, 128.6, 126.2, 118.3, 98.1, 62.9.

HRMS-FIA (m/z) calc'd for C$_{10}$H$_{23}$NO [M+Na]$^+$, 182.0576, found: 182.0577.

(E)-3-Mesitylacrylonitrile (2o)

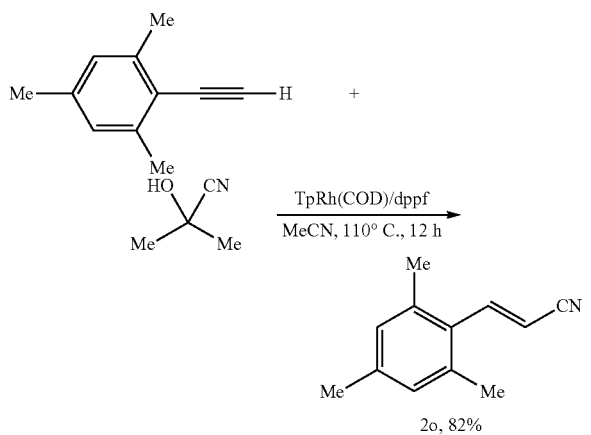

2o, 82%

In an anhydrous, argon-filled glovebox, a 4 mL vial was charged with TpRh(COD) (6.3 mg, 15 μmol, 7.5 mol %), dppf (8.3 mg, 15 μmol, 7.5 mol %), and MeCN (1.5 mL, c=0.13 M). 2-Ethynyl-1,3,5-trimethylbenzene (28.8 mg, 26.5 μL, 0.200 mmol, 1.00 equiv) and acetone cyanohydrin (20.4 mg, 23.5 μL, 0.240 mmol, 1.20 equiv) were then added to the reaction mixture. The vial was sealed with a Teflon cap and moved from the glovebox to a preheated metal heating block (110° C.). The reaction mixture was then stirred at 110° C. for 12 hours. After cooling to 23° C., the resulting mixture was filtered through a short plug of silica gel, eluting with EtOAc. The filtrate was collected and concentrated in vacuo. The resulting residue was purified by flash column chromatography on silica gel, eluting with EtOAc/hexane 1:10 (v/v) to afford 28.1 mg (82%) of the title compound as colorless solid.

Rf=0.50 (EtOAc/hexanes 1:10 (v/v)).

NMR Spectroscopy:

$^1$H NMR (500 MHz, CDCl$_3$, 23° C., δ): 7.58 (d, J=17.0 Hz, 1H), 6.93 (s, 2H), 5.56 (d, J=17.0 Hz, 1H), 2.34 (s, 6H), 2.32 (s, 3H).

$^{13}$C NMR (125 MHz, CDCl$_3$, 23° C., δ): 149.6, 139.4, 136.6, 130.1, 129.5, 118.2, 101.5, 21.1, 21.0.

HRMS-FIA (m/z) calc'd for C$_{12}$H$_{13}$N [M]$^+$, 171.1043; found: 171.1042.

(E)-3-(3-Hydroxyphenyl)acrylonitrile (2p)

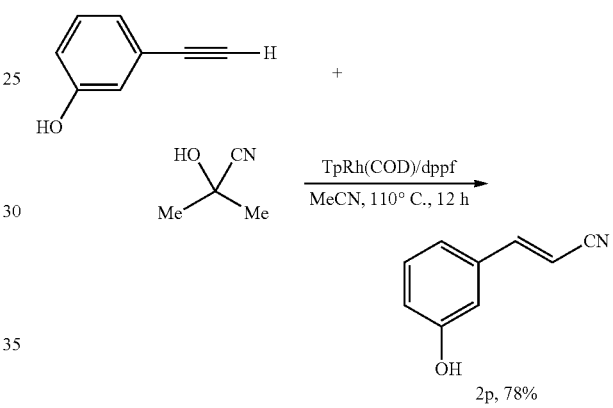

2p, 78%

In an anhydrous, argon-filled glovebox, a 4 mL vial was charged with TpRh(COD) (6.3 mg, 15 μmol, 7.5 mol %), dppf (8.3 mg, 15 μmol, 7.5 mol %), and MeCN (1.0 mL, c=0.2 M) 3-Ethynylphenol (23.6 mg, 0.200 mmol, 1.00 equiv) and acetone cyanohydrin (17.0 mg, 19.5 μL, 0.200 mmol, 1.00 equiv) were then added to the reaction mixture. The vial was sealed with a Teflon cap and moved from the glovebox to a preheated metal heating block (110° C.). The reaction mixture was then stirred at 110° C. for 12 hours. After cooling to 23° C., the resulting mixture was filtered through a short plug of silica gel, eluting with EtOAc. The filtrate was collected and concentrated in vacuo. The resulting residue was purified by flash column chromatography on silica gel, eluting with EtOAc/hexane 1:2 (v/v) to afford 22.6 mg (78%) of the title compound as colorless solid.

Rf=0.35 (EtOAc/hexanes 1:2 (v/v)).

NMR Spectroscopy:

$^1$H NMR (500 MHz, CD$_3$CN, 23° C., δ): 7.43 (d, J=16.5 Hz, 1H), 7.26 (dd, J=8.0 Hz, 8.0 Hz, 1H), 7.20 (br. s, 1H), 7.03 (d, J=8.0 Hz, 1H), 6.97 (s, 1H), 6.90 (dd, J=8.0 Hz, 2.5 Hz, 1H), 6.04 (d, J=16.5 Hz, 1H).

$^{13}$C NMR (125 MHz, CD$_3$CN, 23° C., δ): 158.3, 151.3, 136.3, 131.2, 120.3, 119.3, 119.1, 114.6, 97.6.

HRMS-FIA (m/z) calc'd for C$_9$H$_7$NO [M]$^+$, 145.0525; found: 145.0522.

(E)-3-(6-Methoxy-1-oxo-2,3-dihydro-1H-inden-5-yl) acrylonitrile (2q)

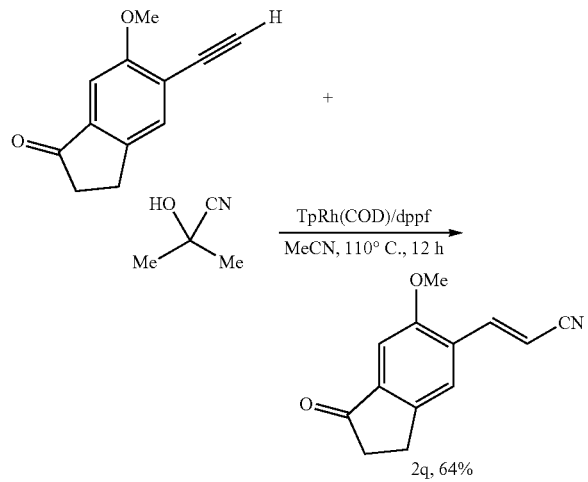

2q, 64%

In an anhydrous, argon-filled glovebox, a 4 mL vial was charged with TpRh(COD) (6.3 mg, 15 μmol, 7.5 mol %), dppf (8.3 mg, 15 μmol, 7.5 mol %), and MeCN (1.0 mL, c=0.2 M). 5-Ethynyl-6-methoxy-2,3-dihydro-1H-inden-1-one (33.2 mg, 0.200 mmol, 1.00 equiv) and acetone cyanohydrin (17.0 mg, 19.5 μL, 0.200 mmol, 1.00 equiv) were then added to the reaction mixture. The vial was sealed with a Teflon cap and moved from the glovebox to a preheated metal heating block (110° C.). The reaction mixture was then stirred at 110° C. for 12 hours. After cooling to 23° C., the resulting mixture was filtered through a short plug of silica gel, eluting with EtOAc. The filtrate was collected and concentrated in vacuo. The resulting residue was purified by flash column chromatography on silica gel, eluting with EtOAc/hexane 1:8 (v/v) to afford 27.3 mg (64%) of the title compound as colorless solid.

Rf=0.50 (EtOAc/hexanes 1:8 (v/v)).

NMR Spectroscopy:

$^1$H NMR (500 MHz, CDCl$_3$, 23° C., δ): 7.67 (d, J=16.8 Hz, 1H), 7.49 (s, 1H), 7.23 (s, 1H), 6.15 (d, J=16.8 Hz, 1H), 3.92 (s, 3H), 3.09 (t, J=11.2 Hz, 2H), 2.73 (t, J=11.2 Hz, 2H).

$^{13}$C NMR (125 MHz, CDCl$_3$, 23° C., δ): 206.3, 157.8, 146.9, 145.6, 139.7, 129.1, 126.3, 118.3, 104.8, 100.1, 56.0, 36.9, 25.0.

HRMS-FIA (m/z) calc'd for C$_{13}$H$_{11}$NO$_2$Na [M+Na]$^+$, 236.0682; found: 236.0683.

(E)-3-(Thiophen-3-yl)acrylonitrile (2r)

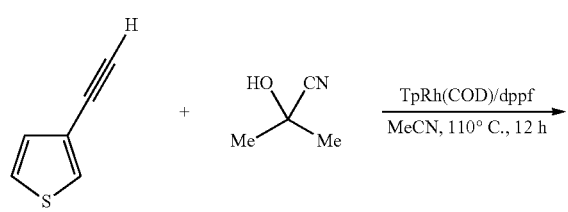

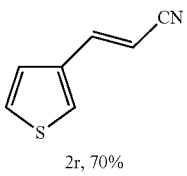

2r, 70%

In an anhydrous, argon-filled glovebox, a 4 mL vial was charged with TpRh(COD) (6.3 mg, 15 μmol, 7.5 mol %), dppf (8.3 mg, 15 μmol, 7.5 mol %), and MeCN (1.0 mL, c=0.2 M) 3-Ethynylthiophene (21.6 mg, 22.0 μL, 0.200 mmol, 1.00 equiv) and acetone cyanohydrin (17.0 mg, 19.5 μL, 0.200 mmol, 1.00 equiv) were then added to the reaction mixture. The vial was sealed with a Teflon cap and moved from the glovebox to a preheated metal heating block (110° C.). The reaction mixture was then stirred at 110° C. for 12 hours. After cooling to 23° C., the resulting mixture was filtered through a short plug of silica gel, eluting with EtOAc. The filtrate was collected and concentrated in vacuo. The resulting residue was purified by flash column chromatography on silica gel, eluting with EtOAc/hexane 1:9 (v/v) to afford 18.9 mg (70%) of the title compound as yellow liquid.

Rf=0.45 (EtOAc/hexanes 1:9 (v/v)).

NMR Spectroscopy:

$^1$H NMR (500 MHz, CDCl$_3$, 23° C., δ): 7.53-7.52 (m, 1H), 7.42-7.39 (m, 2H), 7.27-7.26 (m, 1H), 5.72 (d, J=16.5 Hz, 1H).

$^{13}$C NMR (125 MHz, CDCl$_3$, 23° C., δ): 144.1, 136.8, 128.7, 127.8, 124.3, 118.4, 95.8.

HRMS-FIA (m/z) calc'd for C$_7$H$_5$NSNa [M+Na]$^+$, 158.0034; found: 158.0036.

(E)-3-(Naphthalen-1-yl)acrylonitrile (2s)

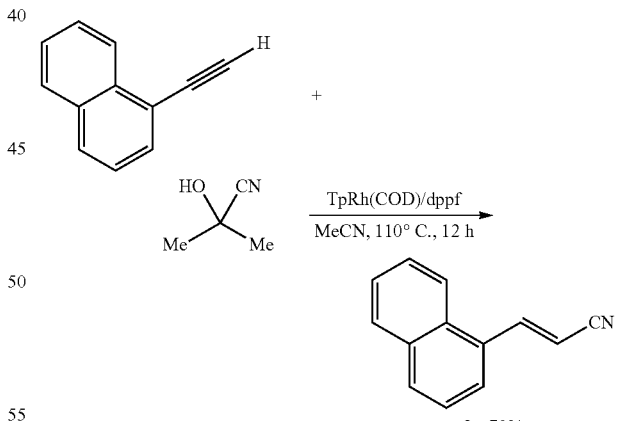

2s, 70%

In an anhydrous, argon-filled glovebox, a 4 mL vial was charged with TpRh(COD) (6.3 mg, 15 μmol, 7.5 mol %), dppf (8.3 mg, 15 μmol, 7.5 mol %), and MeCN (1.5 mL, c=0.13 M). 1-Ethynylnaphthalene (30.4 mg, 0.200 mmol, 1.00 equiv) and acetone cyanohydrin (20.4 mg, 23.5 μL, 0.240 mmol, 1.20 equiv) were then added to the reaction mixture. The vial was sealed with a Teflon cap and moved from the glovebox to a preheated metal heating block (110° C.). The reaction mixture was then stirred at 110° C. for 12 hours. After cooling to 23° C., the resulting mixture was filtered through a short plug of silica gel, eluting with EtOAc. The filtrate was collected and concentrated in vacuo. The resulting residue was purified by flash column chromatography on silica gel, eluting with EtOAc/hexane 1:10 (v/v) to afford 25.1 mg (70%) of the title compound as yellow liquid.

Rf=0.45 (EtOAc/hexanes 1:10 (v/v)).

NMR Spectroscopy:

$^1$H NMR (500 MHz, CDCl$_3$, 23° C., δ): 8.25 (d, J=16.5 Hz, 1H), 8.06 (d, J=8.0 Hz, 1H), 7.95 (d, J=8.5 Hz, 1H), 7.90 (d, J=7.5 Hz, 1H), 7.68 (d, J=7.5 Hz, 1H), 7.62 (t, J=8.0 Hz, 1H), 7.57 (d, J=8.0 Hz, 1H), 7.50 (d, J=7.5 Hz, 1H), 5.98 (d, J=16.5 Hz, 1H).

$^{13}$C NMR (125 MHz, CDCl$_3$, 23° C., δ): 148.1, 133.8, 131.7, 131.1, 130.9, 129.1, 127.6, 126.7, 125.5, 124.8, 123.0, 118.4, 99.0.

HRMS-FIA (m/z) calc'd for C$_{13}$H$_9$N [M]$^+$, 179.0731; found: 179.0729.

(E)-3-(6-Methoxynaphthalen-2-yl)acrylonitrile (2t)

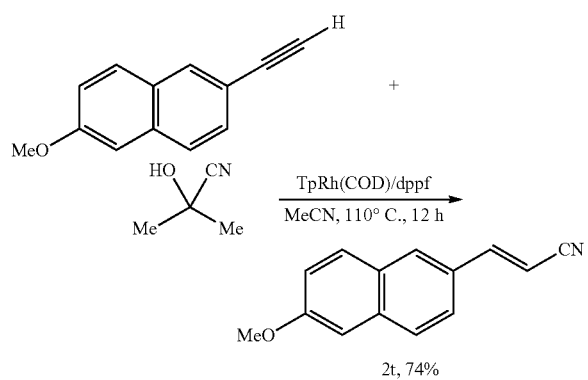

2t, 74%

In an anhydrous, argon-filled glovebox, a 4 mL vial was charged with TpRh(COD) (6.3 mg, 15 μmol, 7.5 mol %), dppf (8.3 mg, 15 μmol, 7.5 mol %), and MeCN (1.5 mL, c=0.13 M). 2-Ethynyl-6-methoxynaphthalene (36.4 mg, 0.200 mmol, 1.00 equiv) and acetone cyanohydrin (20.4 mg, 23.5 μL, 0.240 mmol, 1.20 equiv) were then added to the reaction mixture. The vial was sealed with a Teflon cap and moved from the glovebox to a preheated metal heating block (110° C.). The reaction mixture was then stirred at 110° C. for 12 hours. After cooling to 23° C., the resulting mixture was filtered through a short plug of silica gel, eluting with EtOAc. The filtrate was collected and concentrated in vacuo. The resulting residue was purified by flash column chromatography on silica gel, eluting with EtOAc/hexane 1:9 (v/v) to afford 30.9 mg (74%) of the title compound as yellow solid.

Rf=0.25 (EtOAc/hexanes 1:9 (v/v)).

NMR Spectroscopy:

$^1$H NMR (500 MHz, CDCl$_3$, 23° C., δ): 7.73-7.66 (m, 3H), 7.48 (dd, J=8.9, 2.5 Hz, 1H), 7.44 (d, J=16.5 Hz, 1H), 7.16 (dd, J=8.9, 2.5 Hz, 1H), 7.10 (d, J=2.5 Hz, 1H), 5.86 (d, J=16.5 Hz, 1H), 3.91 (s, 3H).

$^{13}$C NMR (125 MHz, CDCl$_3$, 23° C., δ): 159.2, 150.7, 136.1, 130.3, 129.5, 128.9, 128.4, 127.8, 122.9, 119.9, 118.6, 106.0, 94.9, 55.4.

HRMS-FIA (m/z) calc'd for C$_{14}$H$_{11}$NO [M]$^+$, 209.0837; found 209.0835.

(E)-3-(6-Ethoxypyridin-3-yl)acrylonitrile (2u)

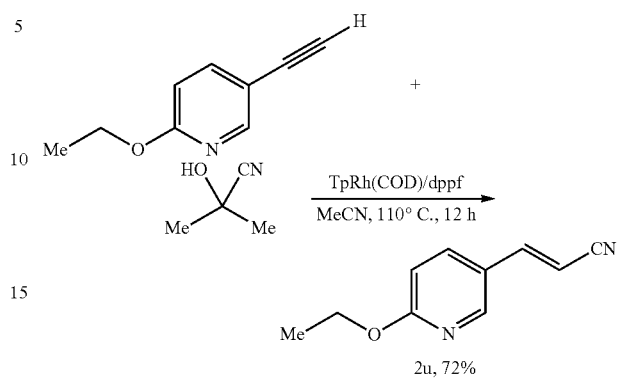

2u, 72%

In an anhydrous, argon-filled glovebox, a 4 mL vial was charged with TpRh(COD) (6.3 mg, 15 μmol, 7.5 mol %), dppf (8.3 mg, 15 μmol, 7.5 mol %), and MeCN (1.0 mL, c=0.2 M). 2-Ethoxy-5-ethynylpyridine (29.4 mg, 22.5 μL, 0.200 mmol, 1.00 equiv) and acetone cyanohydrin (17.0 mg, 19.5 μL, 0.200 mmol, 1.00 equiv) were then added to the reaction mixture. The vial was sealed with a Teflon cap and moved from the glovebox to a preheated metal heating block (110° C.). The reaction mixture was then stirred at 110° C. for 12 hours. After cooling to 23° C., the resulting mixture was filtered through a short plug of silica gel, eluting with EtOAc. The filtrate was collected and concentrated in vacuo. The resulting residue was purified by flash column chromatography on silica gel, eluting with EtOAc/hexane 1:10 (v/v) to afford 25.1 mg (72%) of the title compound as yellow liquid.

Rf=0.20 (EtOAc/hexanes 1:10 (v/v)).

NMR Spectroscopy:

$^1$H NMR (500 MHz, CDCl$_3$, 23° C., δ): 8.18 (d, J=2.5 Hz, 1H), 7.68 (dd, J=8.7, 2.5 Hz, 1H), 7.33 (d, J=16.5 Hz, 1H), 6.75 (d, J=8.7 Hz, 1H), 5.74 (d, J=16.5 Hz, 1H), 4.39 (q, J=7.1 Hz, 3H), 1.39 (t, J=7.1 Hz, 3H).

$^{13}$C NMR (125 MHz, CDCl$_3$, 23° C., δ): 165.6, 148.1, 147.0, 135.4, 122.9, 118.11, 111.9, 94.8, 62.5, 14.5.

HRMS-FIA (m/z) calc'd for C$_{10}$H$_{11}$N$_2$O [M+H]$^+$, 175.0866; found: 175.0868.

(E)-6-Phenylhex-2-enenitrile (5a)

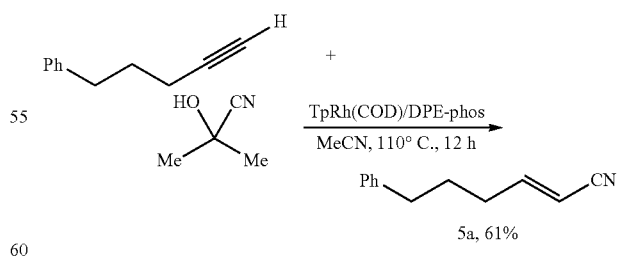

5a, 61%

In an anhydrous, argon-filled glovebox, a 4 mL vial was charged with TpRh(COD) (6.3 mg, 15 μmol, 7.5 mol %), DPE-phos (8.0 mg, 15 μmol, 7.5 mol %) and MeCN (1.0 mL, c=0.2 M). 5-Phenyl-1-pentyne (28.8 mg, 32.0 μL, 0.200 mmol, 1.00 equiv.) and acetone cyanohydrin (17.0 mg, 19.5 μL, 0.200 mmol, 1.00 equiv.) were then added to the reaction mixture. The vial was sealed with a Teflon cap and moved from the glovebox to a preheated metal heating block (110° C.). The reaction mixture was then stirred at 110° C. for 12 hours. After cooling to 23° C., the resulting mixture was filtered through a short plug of silica gel, eluting with EtOAc. The filtrate was collected and concentrated in vacuo. The resulting residue were purified by flash column chromatography on silica gel, eluting with EtOAc/hexane 1:20 (v/v) to afford 20.8 mg (61%) of the title compound as colorless oil.

Rf=0.20 (EtOAc/hexanes 1:20 (v/v)).

NMR Spectroscopy:

$^1$H NMR (500 MHz, CDCl$_3$, 23° C., δ): 7.31-7.28 (m, 2H), 7.22-7.19 (m, 1H), 7.17-7.15 (m, 2H), 6.71 (dt, J=16.5 Hz, 5.0 Hz, 1H), 5.32 (d, J=16.5 Hz, 1H), 2.64 (t, J=5.0 Hz, 2H), 2.27-2.22 (m, 2H), 1.81-1.77 (m, 2H).

$^{13}$C NMR (125 MHz, CDCl$_3$, 23° C., δ): 155.7, 141.2, 128.6, 128.5, 126.2, 117.6, 100.2, 35.1, 32.8, 29.3.

HRMS-FIA (m/z) calc'd for C$_{12}$H$_{13}$N [M+Na]$^+$, 194.0941; found: 194.0940.

(E)-Non-2-enenitrile (5b)

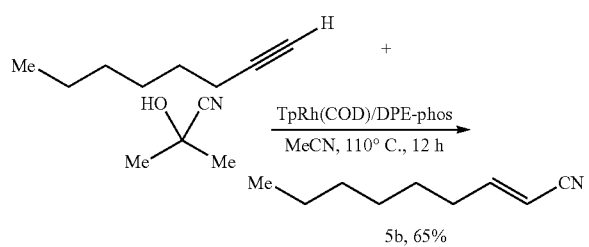

5b, 65%

In an anhydrous, argon-filled glovebox, a 4 mL vial was charged with TpRh(COD) (6.3 mg, 15 μmol, 7.5 mol %), DPE-phos (8.0 mg, 15 μmol, 7.5 mol %) and MeCN (1.0 mL, c=0.2 M). 1-Octyne (22.0 mg, 29.5 μL, 0.200 mmol, 1.00 equiv.) and acetone cyanohydrin (17.0 mg, 19.5 μL, 0.200 mmol, 1.00 equiv.) were then added to the reaction mixture. The vial was sealed with a Teflon cap and moved from the glovebox to a preheated metal heating block (110° C.). The reaction mixture was then stirred at 110° C. for 12 hours. After cooling to 23° C., the resulting mixture was filtered through a short plug of silica gel, eluting with EtOAc. The filtrate was collected and concentrated in vacuo. The resulting residue were purified by flash column chromatography on silica gel, eluting with EtOAc/hexane 1:20 (v/v) to afford 17.8 mg (65%) of the title compound as colorless oil.

Rf=0.20 (EtOAc/hexanes 1:20 (v/v)).

NMR Spectroscopy:

$^1$H NMR (500 MHz, CDCl$_3$, 23° C., δ): 6.71 (dt, J=16.5 Hz, 5.0 Hz, 1H), 5.32 (dt, J=16.5 Hz, 1.5 Hz, 1H), 2.23-2.19 (m, 2H), 1.45-1.42 (m, 2H), 1.32-1.25 (m, 6H), 0.88 (t, J=5.0 Hz, 3H).

$^{13}$C NMR (125 MHz, CDCl$_3$, 23° C., δ): 156.3, 117.7, 99.7, 33.5, 31.6, 28.8, 27.7, 22.6, 14.1.

HRMS-FIA (m/z) calc'd for C$_9$H$_{15}$N [M+Na]$^+$, 160.1097; found: 160.1097.

(E)-3-Cyclohexylacrylonitrile (5d)

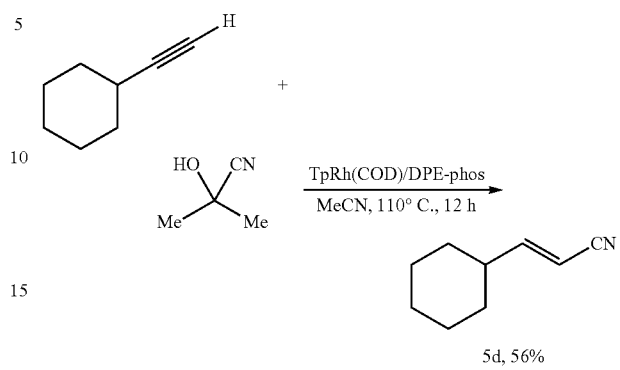

5d, 56%

In an anhydrous, argon-filled glovebox, a 4 mL vial was charged with TpRh(COD) (6.3 mg, 15 μmol, 7.5 mol %), DPE-phos (8.0 mg, 15 μmol, 7.5 mol %) and MeCN (1.0 mL, c=0.2 M). Ethynylcyclohexane (21.6 mg, 23.5 μL, 0.200 mmol, 1.00 equiv.) and acetone cyanohydrin (17.0 mg, 19.5 μL, 0.200 mmol, 1.00 equiv.) were then added to the reaction mixture. The vial was sealed with a Teflon cap and moved from the glovebox to a preheated metal heating block (110° C.). The reaction mixture was then stirred at 110° C. for 12 hours. After cooling to 23° C., the resulting mixture was filtered through a short plug of silica gel, eluting with EtOAc. The filtrate was collected and concentrated in vacuo. The resulting residue were purified by flash column chromatography on silica gel, eluting with EtOAc/hexane 1:20 (v/v) to afford 15.1 mg (56%) of the title compound as colorless oil.

Rf=0.20 (EtOAc/hexanes 1:20 (v/v)).

NMR Spectroscopy:

$^1$H NMR (500 MHz, CDCl$_3$, 23° C., δ): 6.70-6.65 (m, 1H), 5.25 (d, J=16.5 Hz, 1H), 2.17-2.12 (m, 1H), 1.79-1.67 (m, 5H), 1.35-1.11 (m, 5H).

$^{13}$C NMR (125 MHz, CDCl$_3$, 23° C., δ): 161.0, 118.1, 97.7, 41.6, 31.4, 25.8, 25.6.

HRMS-FIA (m/z) calc'd for C$_9$H$_{13}$N [M+Na]$^+$, 158.0941; found: 158.0940.

(E)-3-(Cyclohex-1-en-1-yl)acrylonitrile (5e)

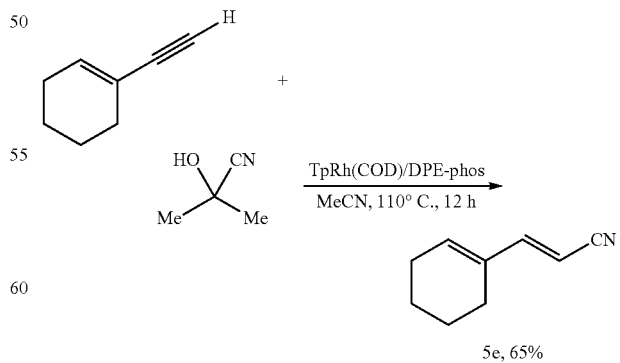

5e, 65%

In an anhydrous, argon-filled glovebox, a 4 mL vial was charged with TpRh(COD) (6.3 mg, 15 μmol, 7.5 mol %), DPE-phos (8.0 mg, 15 μmol, 7.5 mol %) and MeCN (1.0 mL, c=0.2 M). 1-Ethynylcyclohex-1-ene (21.2 mg, 3.5 µL, 0.200 mmol, 1.00 equiv.) and acetone cyanohydrin (17.0 mg, 19.5 µL, 0.200 mmol, 1.00 equiv.) were then added to the reaction mixture. The vial was sealed with a Teflon cap and moved from the glovebox to a preheated metal heating block (110° C.). The reaction mixture was then stirred at 110° C. for 12 hours. After cooling to 23° C., the resulting mixture was filtered through a short plug of silica gel, eluting with EtOAc. The filtrate was collected and concentrated in vacuo. The resulting residue were purified by flash column chromatography on silica gel, eluting with EtOAc/hexane 1:20 (v/v) to afford 17.5 mg (65%) of the title compound as colorless oil.

Rf=0.20 (EtOAc/hexanes 1:20 (v/v)).

NMR Spectroscopy:

$^1$H NMR (500 MHz, CDCl$_3$, 23° C., δ): 6.99 (d, J=16.5 Hz, 1H), 6.15 (t, J=7.5 Hz, 1H), 5.18 (d, J=16.5 Hz, 1H), 2.23 (br. s, 2H), 2.08 (br. s, 2H), 1.72-1.67 (m, 2H), 1.64-1.61 (m, 2H).

$^{13}$C NMR (125 MHz, CDCl$_3$, 23° C., δ): 153.8, 140.1, 134.8, 119.2, 92.5, 26.5, 23.5, 21.9, 21.9.

HRMS-FIA (m/z) calc'd for C$_9$H$_{11}$N [M]$^+$, 133.0886; found: 133.0886.

(E)-3-(Triisopropylsilyl)acrylonitrile (5q)

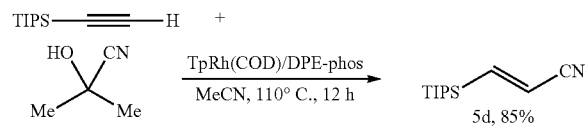

5d, 85%

In an anhydrous, argon-filled glovebox, a 4 mL vial was charged with TpRh(COD) (6.3 mg, 15 µmol, 7.5 mol %), DPE-phos (8.0 mg, 15 µmol, 7.5 mol %) and MeCN (1.0 mL, c=0.2 M). Ethynyltriisopropylsilane (36.4 mg, 46.5 µL, 0.200 mmol, 1.00 equiv.) and acetone cyanohydrin (17.0 mg, 19.5 µL, 0.200 mmol, 1.00 equiv.) were then added to the reaction mixture. The vial was sealed with a Teflon cap and moved from the glovebox to a preheated metal heating block (110° C.). The reaction mixture was then stirred at 110° C. for 12 hours. After cooling to 23° C., the resulting mixture was filtered through a short plug of silica gel, eluting with EtOAc. The filtrate was collected and concentrated in vacuo. The resulting residue were purified by flash column chromatography on silica gel, eluting with EtOAc/hexane 1:20 (v/v) to afford 35.5 mg (85%) of the title compound as colorless oil.

Rf=0.25 (EtOAc/hexanes 1:20 (v/v)).

NMR Spectroscopy:

$^1$H NMR (500 MHz, CDCl$_3$, 23° C., δ): 7.04 (d, J=20.0 Hz, 1H), 5.97 (d, J=20.0 Hz, 1H), 1.16-1.04 (m, 21H).

$^{13}$C NMR (125 MHz, CDCl$_3$, 23° C., δ): 155.3, 117.8, 114.0, 134.8, 18.5, 10.6.

HRMS-FIA (m/z) calc'd for C$_{12}$H$_{23}$NSi [M+Na]$^+$, 232.1492, found: 232.1492.

TpRh(COD)

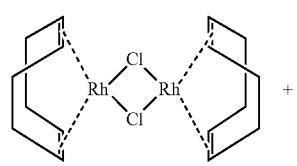

+

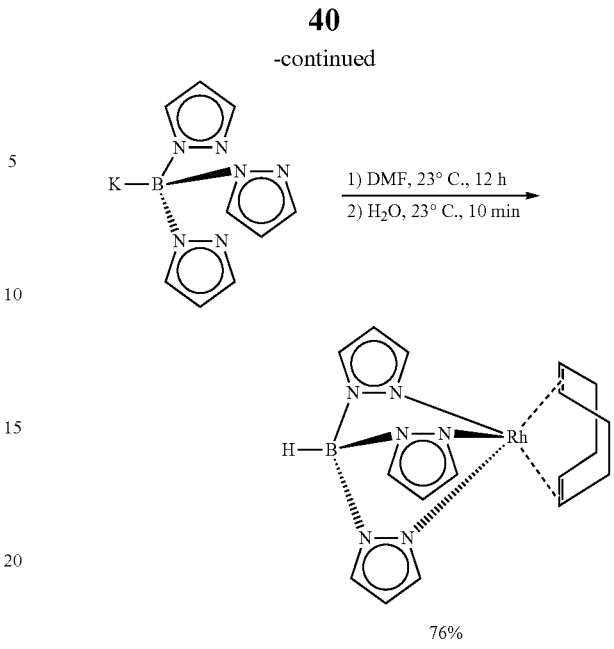

76%

According to a literature procedure$^{15}$, under argon atmosphere, a 100-mL flask was charged with bis(1,5-cyclooctadiene)rhodium(I) chloride dimer (1.0 g, 2.0 mmol, 1.0 equiv) and KTp (2.0 g, 4.0 mmol, 2.0 equiv), to which DMF (15 mL, c=0.13 M) was added. After the reaction mixture was stirred at 23° C. for 12 h, 30 mL of water was added to the mixture, the resulting suspension was stirred for further 10 min. Then the reaction mixture was filtered, and the filter cake was purified by flash column chromatography on neutral alumina, eluting with methylene dichloride. The yellow band was collected, and the volatiles was evaporated to give 1.3 g (76%) of TpRh(COD) as yellow powder.

NMR Spectroscopy:

$^1$H NMR (500 MHz, CDCl$_3$, 23° C., δ): 7.77 (br. s, 3H), 7.59 (br. s, 3H), 6.21 (br. s, 3H), 3.87 (br. s, 4H), 2.60-2.58 (m, 4H), 1.93-1.88 (m, 4H), proton of B—H is missing.

$^{13}$C NMR (125 MHz, CDCl$_3$, 23° C., δ): 139.5, 134.9, 104.9, 73.5, 73.4, 31.3.

$^{11}$B NMR (128 MHz, CDCl$_3$, 23° C., δ): -3.57 (d, J=113 Hz).

HRMS-FIA (m/z) calc'd for C$_{17}$H$_{23}$BN$_6$Rh [M+H]$^+$, 425.1127, found: 425.1127.

TpRh(dppf)

-continued

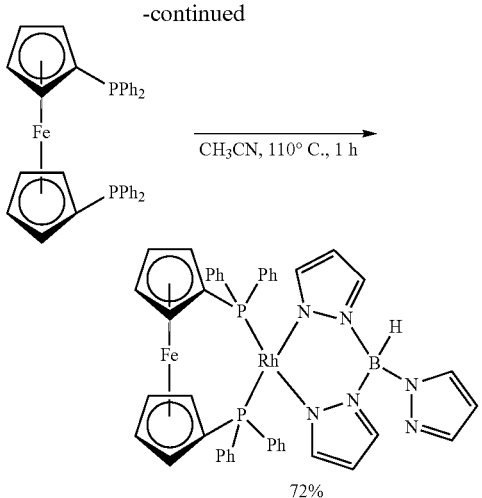

CH₃CN, 110° C., 1 h

72%

In an anhydrous, argon-filled glovebox, a 4 mL vial was charged with TpRh(COD) (12.7 mg, 0.0300 mmol, 1.00 equiv) and dppf (16.9 mg, 0.0300 mmol, 1.00 equiv).

After adding 1.0 mL of MeCN to the reaction mixture, the vial was sealed with a Teflon cap and moved out of the glovebox to a preheated metal heating block at 110° C. After 1 hour, the resulting mixture was cooled to 23° C. Orange crystals precipitated from the solution within 1 hour. The vial was then placed in a 4° C. fridge for 12 hours. After warming the solution to 23° C., 18.8 mg (72%) of crystals were obtained by careful filtration. The quality of the crystals was suitable for X-ray crystallographic analysis. The compound has a limited lifetime in solution. In solid state, TpRh(dppf) can be oxidized by air.

NMR Spectroscopy:

$^1$H NMR (500 MHz, CD$_2$Cl$_2$, 23° C., δ): 7.77-7.58 (br. m, 10H), 7.23-6.93 (br. m, 16H), 6.24 (br. s, 1H), 5.74 (br. s, 1H), 5.42 (br. s, 1H), 4.13-3.89 (br. m, 9H).

$^{13}$C NMR (125 MHz, CD$_2$Cl$_2$, 23° C., δ): 141.3, (d, J=153.5 Hz), 136.5-136.0 (br, m), 134.8 (br, s), 134.1, 133.3-132.4 (br, d), 128.5, 126.7, 103.2, 78.8-78.5 (br, m), 75.1-73.9 (br, m), 71.4.

$^{31}$P NMR (202 MHz, CD$_2$Cl$_2$, 23° C., δ): 46.5 (d, J=183 Hz), 44.7 (d, J=183 Hz).

$^{11}$B NMR (128 MHz, CD$_2$Cl$_2$, 23° C., δ): −1.28 (br. s).

HRMS-FIA (m/z) calc'd for C$_{43}$H$_{38}$BFeN$_6$P$_2$Rh [M+H]$^+$, 871.1214, found: 871.1204.

The invention claimed is:

1. A process for hydrocyanation of terminal alkynes comprising reacting a terminal alkyne (I) with at least one —CN source selected from the group consisting of HCN and cyanohydrine (II) in the presence of a Rh-complex to obtain an E-alkenyl nitrile (III):

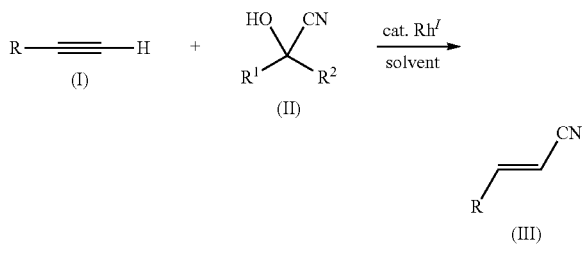

wherein R is i) a straight chain, branched chain or cyclic aliphatic C$_1$ to C$_{20}$ hydrocarbon, optionally having one or more unsaturated bonds, C$_3$-C$_8$-heterocycloalkyl, C$_6$ to C$_{20}$ aryl, (C$_1$-C$_6$)-alkyl-C$_6$ to C$_{20}$-aryl, (C$_1$-C$_6$)-alkyl-C$_5$ to C$_{20}$-heteroaryl, each hydrocarbon optionally being substituted by one or more groups selected from C$_1$ to C$_{20}$ straight chain, branched chain or cyclic aliphatic hydrocarbons, optionally having one or more unsaturated bonds, C$_3$-C$_8$-heterocycloalkyl, C$_6$ to C$_{20}$ aryl, (C$_1$-C$_6$)-alkyl-C$_6$ to C$_{20}$-aryl, (C$_1$-C$_6$)-alkyl-C$_5$ to C$_{20}$-heteroaryl or heterosubstituents; or ii) SiR$^I$R$^{II}$R$^{III}$, wherein R$^I$, R$^{II}$, and R$^{III}$ may be same or different and each stands for a straight chain, branched chain or cyclic aliphatic C$_1$ to C$_{20}$ hydrocarbon, optionally having one or more unsaturated bonds, C$_3$-C$_8$-heterocycloalkyl, C$_6$ to C$_{20}$ aryl, (C$_1$-C$_6$)-alkyl-C$_6$ to C$_{20}$-aryl, C$_5$ to C$_{20}$-heteroaryl, (C$_1$-C$_6$)-alkyl-C$_5$ to C$_{20}$-heteroaryl, each hydrocarbon optionally being substituted by one or more groups selected from C$_1$ to C$_{20}$ straight chain, branched chain or cyclic aliphatic hydrocarbons, optionally having one or more unsaturated bonds, C$_3$-C$_8$-heterocycloalkyl, C$_6$ to C$_{20}$ aryl, (C$_1$-C$_6$)-alkyl-C$_6$ to C$_{20}$-aryl, (C$_1$-C$_6$)-alkyl-C$_5$ to C$_{20}$-heteroaryl or heterosubstituents;

wherein R$_1$ and R$_2$ may be same or different and each stands for a straight chain, branched chain or cyclic aliphatic C$_1$ to C$_{20}$ hydrocarbon, optionally having one or more unsaturated bonds, C$_3$-C$_8$-heterocycloalkyl, C$_6$ to C$_{20}$ aryl, (C$_1$-C$_6$)-alkyl-C$_6$ to C$_{20}$-aryl, (C$_1$-C$_6$)-alkyl-C$_5$ to C$_{20}$-heteroaryl, each hydrocarbon optionally being substituted by one or more groups selected from C$_1$ to C$_{20}$ straight chain, branched chain or cyclic aliphatic hydrocarbons, optionally having one or more unsaturated bonds, C$_3$-C$_8$-heterocycloalkyl, C$_6$ to C$_{20}$ aryl, (C$_1$-C$_6$)-alkyl-C$_6$ to C$_{20}$-aryl, (C$_1$-C$_6$)-alkyl-C$_5$ to C$_{20}$-heteroaryl or heterosubstituents;

wherein cat Rh$^I$ stands for a Tp-Rhodium complex with a mono- or bidentate phosphine, and wherein solvent stands for an organic solvent.

2. Process for hydrocyanation of terminal alkynes according to claim 1, wherein R is a straight chain, branched chain or cyclic aliphatic C$_1$ to C$_{20}$ hydrocarbon, optionally having one or more unsaturated bonds, C$_6$ to C$_{20}$ aryl, (C$_1$-C$_6$)-alkyl-C$_6$ to C$_{20}$-aryl, each hydrocarbon optionally being substituted by one or more heterosubstituents.

3. Process for hydrocyanation of terminal alkynes according to claim 1, wherein R$_1$ and R$_2$ may be same or different and each stands for is a straight chain, branched chain or cyclic aliphatic C$_1$ to C$_{20}$ hydrocarbon, optionally having one or more unsaturated bonds, C$_6$ to C$_{20}$ aryl, (C$_1$-C$_6$)-alkyl-C$_6$ to C$_{20}$-aryl, each hydrocarbon optionally being substituted by one or more heterosubstituents.

4. Process for hydrocyanation of terminal alkynes according to claim 1, wherein cat Rh$^I$ stands for a Tp-Rhodium complex with a bidentate phosphine whereby the residues of the Tp ((tris(1-pyrazolyl)borate anion) and/or the bidentate phosphine ligand are optionally substituted with electro-donating substituent(s).

5. Tp-Rhodium complex with a bidentate phosphine ligand whereby the residues of the Tp ((tris(1-pyrazolyl) borate anion) and/or the bidentate phosphine ligand are optionally substituted with electro-donating substituent(s).

6. Tp-Rhodium complex with a mono- or bidentate phosphine ligand whereby the mono- or bidentate phosphine ligand is selected from dppf (1,1'-bis(diphenylphosphino) ferrocene), dppm (1-bis(diphenylphosphino)methane), dppe (bis(diphenylphosphino)ethan), xantphos (4,5-bis(diphenylphosphino)-9,9-dimethylxanthene), PCy$_3$ (tricyclohexylphosphine), PPh$_3$ (triphenylphosphine), BINAP (2,2' bis (diphenylphosphino)-1,1'-binaphthyl), and DPE-phos (bis[2-(diphenylphosphino) phenyl]ether.

7. Tp-Rhodium complex with a bidentate phosphine ligand according to claim 6, which is selected from TpRh(dppf) or TpRh(dpe-phos).

\* \* \* \* \*